US011426610B2

(12) United States Patent
Puleo et al.

(10) Patent No.: US 11,426,610 B2
(45) Date of Patent: Aug. 30, 2022

(54) NEUROMODULATION TECHNIQUES FOR PERTURBATION OF PHYSIOLOGICAL SYSTEMS

(71) Applicant: General Electric Company, Schenectady, NY (US)

(72) Inventors: Christopher Michael Puleo, Niskayuna, NY (US); Victoria Eugenia Cotero, Troy, NY (US); Jeffrey Michael Ashe, Gloversville, NY (US); John Frederick Graf, Ballston Lake, NY (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 497 days.

(21) Appl. No.: 16/399,692

(22) Filed: Apr. 30, 2019

(65) Prior Publication Data

US 2020/0346043 A1 Nov. 5, 2020

(51) Int. Cl.
*A61N 7/00* (2006.01)
*A61N 1/05* (2006.01)
*A61N 1/36* (2006.01)

(52) U.S. Cl.
CPC ............. *A61N 7/00* (2013.01); *A61N 1/0536* (2013.01); *A61N 1/36017* (2013.01); *A61N 2007/0026* (2013.01); *A61N 2007/0073* (2013.01); *A61N 2007/0078* (2013.01)

(58) Field of Classification Search
CPC .... A61N 7/00; A61N 1/0536; A61N 1/36017; A61N 2007/0026; A61N 2007/0073; A61N 2007/0078; A61N 2007/0021; A61B 5/14546; A61B 5/6823; A61B 5/4244; A61B 5/14532; A61B 5/4836; A61B 5/686; A61B 5/425; A61B 5/416; A61B 5/14503; A61B 5/0051
See application file for complete search history.

(56) References Cited

U.S. PATENT DOCUMENTS

| 6,615,081 B1 | 9/2003 | Boveja |
| 8,591,419 B2 | 11/2013 | Tyler |
| 2006/0073097 A1 | 4/2006 | Ma et al. |
| 2012/0271133 A1 | 10/2012 | Gal et al. |

(Continued)

FOREIGN PATENT DOCUMENTS

| WO | WO2015069446 A1 | 5/2015 |
| WO | 2016072875 A1 | 5/2016 |

(Continued)

OTHER PUBLICATIONS

International Application No. PCT/IB2020/054901—International Search Report and Written Opinion dated Aug. 18, 2020.

(Continued)

*Primary Examiner* — Hien N Nguyen
(74) *Attorney, Agent, or Firm* — Fletcher Yoder, P.C.

(57) ABSTRACT

Embodiments of the present disclosure relate to techniques for inducing physiological perturbations in a subject via neuromodulation, e.g., peripheral neuromodulation of a region of interest of an organ. The nature and degree of the perturbations may be related to the subject's clinical condition. Accordingly, an assessment of one or more characteristics of the perturbations may be used to determine a clinical condition of the subject.

17 Claims, 14 Drawing Sheets

(56) References Cited

U.S. PATENT DOCUMENTS

| | | | |
|---|---|---|---|
| 2013/0184728 A1 | 7/2013 | Mishelevich | |
| 2016/0236012 A1 | 8/2016 | Zderic et al. | |
| 2017/0100605 A1 | 4/2017 | Schwab et al. | |
| 2017/0333708 A1* | 11/2017 | Conde | A61N 1/36085 |
| 2018/0028841 A1* | 2/2018 | Konofagou | A61N 7/00 |
| 2019/0117977 A1 | 4/2019 | Puleo et al. | |

FOREIGN PATENT DOCUMENTS

| | | |
|---|---|---|
| WO | 2018081763 A1 | 5/2018 |
| WO | 2018081826 A1 | 5/2018 |
| WO | WO2018081826 A1 | 5/2018 |

OTHER PUBLICATIONS

International Application No. PCT/US2020/038665—International Search Report and Written Opinion dated Nov. 5, 2020.
Castellanos et al., "Ultrasound Stimulation of Insulin Release from Pancreatic Beta Cells as a Potential Novel Treatment for Type 2 Diabetes," Ultrasound Medical Biology, vol. 43 Issue: 6 pp. 1210-1222, Jun. 2017.
International Application No. PCT/US2017/059394—International Search Report and Written Opinion dated Feb. 13, 2018.

* cited by examiner

NEUROMODULATION TECHNIQUES FOR PERTURBATION OF PHYSIOLOGICAL SYSTEMS

STATEMENT REGARDING FEDERALLY SPONSORED RESEARCH & DEVELOPMENT

This invention was made with government support under contract number HR0011-18-C-0040 awarded by the Defense Advanced Research Projects Agency (DARPA). The government has certain rights in the invention.

BACKGROUND

The subject matter disclosed herein relates to techniques to assess physiological systems via intentional perturbation of such systems and assessment of recovery from and/or characteristics of the perturbation. In particular, the perturbation may be the result of targeted neuromodulation.

Healthcare providers use a variety of methods to test for and diagnose clinical conditions. In certain cases, a subject may be subjected to conditions that induce a stress or perturbation of some kind, and an assessment of the subject's response to the stress or perturbation may be indicative of a clinical condition or overall health. Such perturbations may be induced by exercise, pharmacologic agents, fasting, etc. For example, a glucose tolerance test may involve administering a glucose load to a subject and assessing blood samples taken from the subject after the administration to determine how the subject responds. However, such testing is complex and may require dietary restrictions (e.g., fasting in advance) with which some subjects may not comply, which in turn may influence the results. Further, administration of pharmacologic agents may involve undesirable side effects. Accordingly, improved techniques for diagnosing certain clinical conditions would be beneficial.

BRIEF DESCRIPTION

The disclosed embodiments are not intended to limit the scope of the claimed subject matter, but rather these embodiments are intended only to provide a brief summary of possible embodiments. Indeed, the disclosure may encompass a variety of forms that may be similar to or different from the embodiments set forth below.

In one embodiment, a modulation system is provided that includes an energy application device configured to apply energy to a region of interest to cause a physiological perturbation in a subject. The system also includes a controller configured to control application of the energy via the energy application device to the region of interest to induce the physiological perturbation to cause a change in concentration of one or more molecules of interest relative to a baseline concentration. The controller is also configured to receive information indicative of the concentration of the one or more molecules of interest and determine that the subject is in is in category selected from two or more categories based on a change in the concentration of the one or more molecules of interest relative to the baseline concentration within a time period.

In another embodiment, a method of inducing a physiological perturbation in a subject is provided. The method includes the steps of directing an energy application device at a region of interest of a subject; applying the energy to the region of interest to modulate activity of at least one axon terminal within the region of interest as a result of the applying; assessing one or more characteristics of the perturbation at one or more time points after the perturbation; and providing an indication of a clinical condition of the subject based on the assessing.

In another embodiment, a modulation system is provided that includes an energy application device configured to apply energy to a first region of interest in a first organ and to a second region of interest in a second organ. The system also includes a controller configured to control a first application of the energy via the energy application device to the first region of interest to cause a first perturbation as a result of the first application of the energy; receive information indicative of a first perturbation characteristic; control a second application of the energy via the energy application device to the second region of interest to cause a second perturbation as a result of the second application of the energy; receive information indicative of a second perturbation characteristic; determine a clinical condition of the subject based on the first perturbation characteristic and the second perturbation characteristic; and provide an indication of the clinical condition.

In another embodiment, a method of assessing a physiological perturbation in a subject is provided. The method includes the steps of applying ultrasound energy to a region of interest in a subject to cause an approximated fasting state in the subject via neuromodulation; receiving glucose and insulin concentration data from the subject in the approximated fasting state; applying the data to a model, wherein the model is based on a relationship between glucose and insulin concentration in the approximated fasting state for a plurality of normal subjects; receiving an indication of an insulin resistance of the subject using the model; and providing a treatment recommendation based on the indication.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
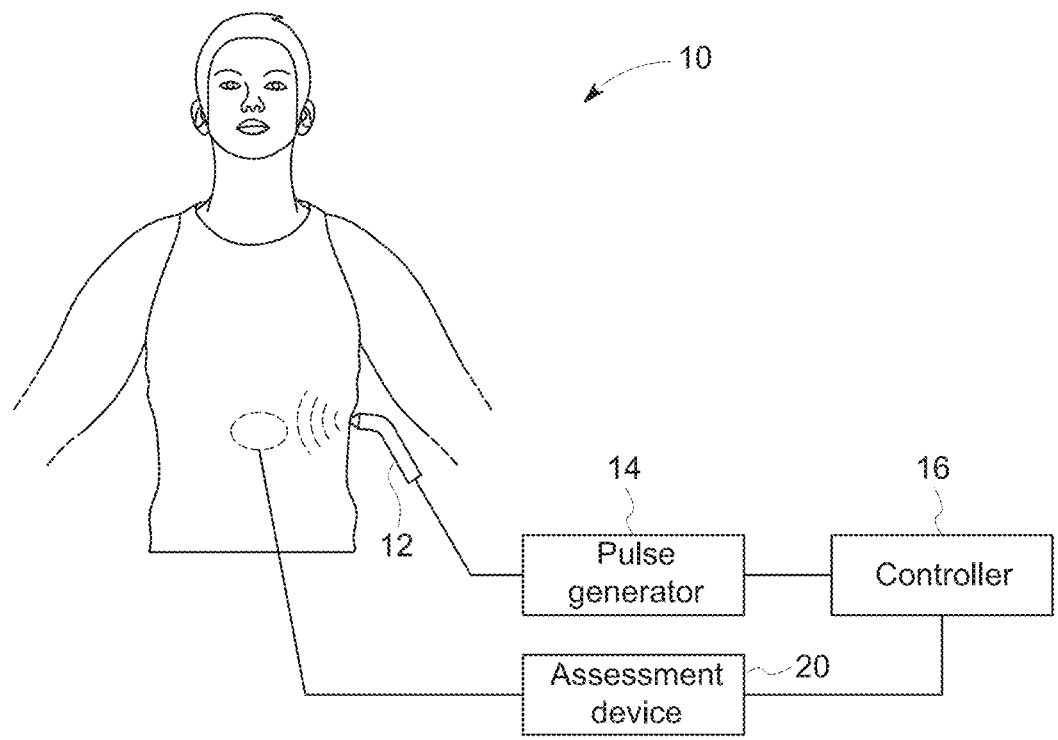
FIG. 1 is a schematic representation of a neuromodulation system using a pulse generator according to embodiments of the disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to: "for example," "for instance," "such as," "e.g.," "including," "in certain embodiments", "in some embodiments", and "in one (an) embodiment."

Provided herein are techniques for physiological perturbation via neuromodulation of targeted regions of interest and to cause targeted physiological perturbations that are the result of the modulation. Such physiological perturbations may be useful for assessing subject responses to the perturbations in a controlled environment. For example, a physiological perturbation may cause metabolic pathways to adjust to the effects of the perturbation to achieve homeostasis. The quality or effectiveness of the response may be a measure of a subject's overall condition. In one embodiment, neuromodulation is used alternatively or additionally relative to other techniques for inducing physiological changes (e.g., exercise stress tests, pharmacologic agent administration). While pharmacologic agents may perturb physiological systems, their effects may vary from subject to subject due to variability in patient comorbidities or variability in physiological processes that respond to the agents and that are unconnected to the systems being examined. For example, certain subjects may metabolize pharmacologic agents at different rates due to pharmacogenetic differences in drug metabolism pathways. Differences in metabolism rates may lead to differences in agent effects. Accordingly, such tests using pharmacologic agents may fail to identify patients with certain clinical conditions. That is, certain patients may have responses that are difficult to fit to existing indices or models of response types.

Neuromodulation applied to cause physiological perturbations may be targeted, allowing healthcare providers to induce desired changes and assess one or more characteristics of the perturbation. Such characteristics may include a change in concentration of one or more molecules of interest in response to the perturbation and a time to recovery (e.g., an assessment of the persistence of the physiological perturbation). Accordingly, the assessed characteristic of the perturbation may be a change in concentration of one or more molecules of interest over a predetermined time period and/or a total time to achieve a predetermined baseline concentration of one or more molecule of interest. In certain embodiments, based on the assessment, a diagnosis of a clinical condition may be made and/or treatment or treatment recommendation to the subject may be provided.

Neuromodulation of regions of interest may cause physiological perturbations in healthy or diseased subjects. In one embodiment, neuromodulation that does not cause a characteristic change in a subject may be associated with a clinical condition or a disease diagnosis. In another embodiments, different clinical conditions or categories may be associated with certain characteristic responses to the neuromodulation. That is, application of energy to a region of interest and the absence of predicted physiological responses to the perturbation may be indicative of diseased organs, including metabolic or inflammatory/anti-inflammatory pathways that are unable to respond to neuromodulation in a manner of a healthy patient. In one example, neuromodulating energy applied to pancreas with no resultant increase in circulating insulin levels is indicative of a nonresponsive subject who can no longer produce insulin. Therefore, a treatment recommendation may be provided that neuromodulation therapy will not work and insulin should be provided.

While perturbations may be induced by challenges such as exercise, administration of pharmacologic agents, and/or dietary changes (fasting), such perturbations are typically diffuse and untargeted. In contrast, as provided herein, neuromodulation may be targeted to one or more specific structures in the body to cause targeted or predictable physiological perturbations. Further, insofar as multiple organs may be involved in metabolic processes, neuromodulation of one or more regions of interest in specific organs may be beneficial for identifying parts of a pathway that may be dysfunctional.

As provided herein, neuromodulation may induce physiological perturbation via modulation of activity at axon terminals within the region of interest. The targeted region or regions of interest may be any tissue or structure in the body having axon terminals forming synapses with non-neuronal cells or fluids. In one example, the region of interest may be in an organ or structure, such as a spleen, liver, pancreas, or gastrointestinal tissue. In another example, the regions of interest may be in a lymph system tissue. Neuromodulation of regions of interest permits a local, limited, and nonablative application of energy to only the targeted regions of interest and without the energy being applied outside of the regions of interest. Energy application may trigger efferent perturbations outside of the targeted regions of interest, e.g., in the same organ, tissue or structure containing the region of interest or in other organs and structures that do not contain the targeted region of interest. In some embodiments, the afferent effects may be induced in areas of a hypothalamus by way of example. The energy application may also induce afferent effects along the targeted nerve upstream from the site of the energy application. In some embodiments, the effects outside of the targeted region/s of interest may be achieved without direct energy application to areas outside of the region/s of interest where the effects are induced. Accordingly, local energy application may be used to realize or achieve systemic perturbations which may include local effects, downstream effects and/or upstream effects.

The disclosed techniques may be used to exert perturbations of physiological processes of the body using an external or extracorporeal source to cause targeted physiological perturbations in subjects. Via neuromodulation to the targeted regions of interest, physiological processes may be altered, slowed, halted, or reversed. Also provided herein are techniques that may be applied to subjects to upset or temporarily challenge the dynamic equilibrium or homeostasis of physiological processes, such as glucose regulation; or to stimulate the physiological system back into a homeostatic state. Neuromodulation to the targeted regions of interest may exert a change in physiological processes to interrupt, decrease, or augment one or more physiological pathways in a subject to yield the desired physiological perturbation.

The neuromodulation techniques discussed herein may be used to cause a physiological perturbation in the neuromodulated subject. The physiological perturbation may include local changes in the region of interest or tissue to which the energy was applied as well as systemic changes that are the result of the neuromodulation. In certain embodiments, one or more characteristics of the perturbation may be assessed as part of the present techniques. These changes may include changes in one or more molecules of interest, changes in physiological parameters of the subject, displacement, enlargement, or other morphological changes to one or more tissue structures of the subject, changes in cell populations in the subject, a change in flow parameters of blood or other fluids, etc. In one embodiment, the physiological perturbation causes a change in concentration (e.g., increased, decreased) of a molecule of interest and/or a change in characteristics of a molecule of interest. That is, the perturbation may include selective modulation of the tissue production or release of one or more molecules of interest (e.g., a first molecule of interest, a second molecule of interest, and so on) and may refer to modulating or influencing a concentration (circulating, tissue) or characteristics (covalent modification) of a molecule as a result of energy application to one or more regions of interest (e.g., a first region of interest, a second region of interest, and so on) in one or more tissues (e.g., a first tissue, a second tissue, and so on). Modulation of a molecule of interest may include changes in characteristics of the molecule such as expression, secretion, translocation of proteins and direct activity changes. Modulation may be driven based on the effect of the applied energy on ion channel either driving nerve activity and function itself or modulation of neighboring non-neuronal cells as a result of molecules derived from the neural activity or direct activation within the non-neuronal cell. Modulation of a molecule of interest may also refer to maintaining a desired concentration of the molecule, such that expected changes or fluctuations in concentration do not occur as a result of the neuromodulation. Modulation of a molecule of interest may refer to causing changes in molecule characteristics, such as enzyme-mediated covalent modification (changes in phosphorylation, acetylation, ribosylation, etc.). That is, it should be understood that selective modulation of a molecule of interest may refer to molecule concentration and/or molecule characteristics. The molecule of interest may be a biological molecule, such as one or more of carbohydrates (monosaccharaides, polysaccharides), lipids, nucleic acids (DNA, RNA), or proteins. In certain embodiments, the molecule of interest may be a signaling molecule such as a hormone (an amine hormone, a peptide hormone, or a steroid hormone).

Certain embodiments described herein provide neuromodulation techniques for the diagnosis of metabolic dysfunction. In one embodiment, the diagnosis may be a presence or absence of glucose metabolism dysfunction and associated disorders. Glucose regulation is complex and involves different local and systemic metabolic pathways. Application of energy to targeted region/s of interest causes characteristic changes in these metabolic pathways that affect glucose regulation. In some embodiments, modulation at one or more regions of interest may be used to identify disorders including but not limited to, diabetes (i.e., type 1 or type 2 diabetes), hyperglycemia, hyperlipidemia, sepsis, trauma, infection, physiological stress, diabetes-associated dementia, obesity, or other eating or metabolic disorders. In one example, physiological stress may be medically defined to include a variety of acute medical conditions (infection, severe injury/trauma, heart attack, bypass) as well as surgical instances with presentation of hyperglycemia. The targeted perturbation via neuromodulation may induce changes in glucoregulatory hormones in the blood or tissue to cause a deviation from glucose concentration. The targeted perturbation via neuromodulation may also induce changes in activity of sensory or effector neurons within the metabolic physiological control system, and response of this system may be analyzed by imaging (e.g., MRI) or electrically recording (e.g., ECG) or other physiological monitoring. The change to these systems as a result of neuromodulation may be different in healthy versus diseased patients. In a healthy subject, the perturbation may be cleared over time such that glucose concentration returns to normal. Further, physiological perturbations may be used to identify subjects without a disease diagnosis, but who are pre-diabetic. In one embodiment, the physiological perturbation is used to identify subjects with insulin resistance, who may or may not be identified as diabetic.

Certain embodiments described herein provide neuromodulation techniques for the diagnosis of control of inflammation and immune function and associated disorders. Regulation of the inflammatory and activity status of immune cells involves different local and systemic neural, humoral, and cellular pathways. Application of energy to targeted region/s of interest causes characteristic changes in these inflammatory and anti-inflammatory pathways that affect circulating cytokine and neurotransmitter concentrations and therefore immune cell activity and states. In some embodiments, modulation at one or more regions of interest may be used to identify disorders including but not limited to, rheumatoid arthritis, irritable bowel disease, psoriasis, or other chronic inflammatory or related disorders. The targeted perturbation via neuromodulation may induce changes in immune markers such as inflammatory cytokine, hormones, or neurotransmitters in the blood or tissue to cause activity changes in resident or circulating immune cells. The targeted perturbation via neuromodulation may also induce changes in activity of sensory or effector neurons within the inflammatory control systems, and response of this system may be analyzed by imaging or electrically recording. The change to these systems as a result of neuromodulation may be different in healthy versus diseased patients. In a healthy patient, the perturbations may cause temporary changes to physiology or changes that are lower in magnitude, while in diseased patients the perturbations may be longer lasting. Further, physiological perturbations may be used to identify patients without a current disease diagnosis, or who are pre-symptomatic or developing a chronic inflammatory disease.

To that end, the present techniques relate to targeted modulation of synapses at axon terminals in a tissue via a direct application of energy by an energy source to cause a change that results in a measurable physiological perturbation (e.g., a change in a circulating molecule concentration or a suite of concentrations changes forming a characteristic physiological profile). The targeted synapses may include axoextracellular synapses formed between presynaptic axon terminals and postsynaptic non-neuronal cells. In addition, while certain disclosed embodiments are discussed in the context of axoextracellular synapses, it should be understood that the axon terminals may form axosecretory, axosynaptic, axosomatic or axoextracellular synapses, and that additionally or alternatively, these synaptic types are contemplated as being selectively modulated, as provided herein. Further, certain axon terminals may terminate in interstitial or body fluid that may also experience neurotransmitter release as a result of the modulation. The disclosed synapses may be modulated to alter an activity in the synapses, e.g., a release of neurotransmitters from the presynaptic axon terminals, as a result of the energy application. Accordingly, the altered activity may lead to local effects and/or non-local (e.g., systemic) effects to cause the overall profile of physiological changes associated with the desired or targeted physiological perturbation. The present techniques permit energy to be focused in a targeted manner on a volume of tissue that includes certain axon terminals to preferentially directly activate the targeted axon terminals to achieve desired physiological perturbations. In this manner, the targeted axon terminals within a region of interest are activated while, in certain embodiments, axon terminals in the same organ or tissue structure but that are outside of the region of interest are not activated. Because organs and tissue structures may include different types of axon terminals that form synapses with different types of postsynaptic non-neuronal cells, the region of interest may be selected that includes particular types of axon terminals that, when activated, yield the desired targeted physiological perturbation. Accordingly, the modulation may target a specific type of axon terminal on the basis of the presynaptic neuron type, the postsynaptic cell type, or both.

For example, in one embodiment, the type of axon terminal may be an axon terminal forming an axoextracellular synapse with a resident (i.e., tissue-resident or non-circulating) liver, pancreatic, or gastrointestinal tissue cell. That is, the axoextracellular synapse is formed at a junction between an axon terminal and a nonneuronal cell or interstitial or body fluid. Accordingly, the application of energy leads to modulation of function in the region of interest. However, it should be understood that, based on the population of axon terminal types and the characteristics of the presynaptic neuron type and postsynaptic cells (e.g., immune cells, lymph cells, mucosal cells, muscle cells, etc.) of the axoextracellular synapse, different targeted physiological effects may be achieved. Further, as noted, the axon terminals may terminate in interstitial or body fluid that may also experience neurotransmitter release as a result of the modulation. Accordingly, applying energy to a region of interest in a tissue of a subject may activate axon terminals (and, where applicable, their associated axoextracellular synapse) within the region of interest while untargeted axon terminals (and associated synapses) outside of the region of interest may be unaffected. However, because modulation may result in systemic effects, untargeted axon terminals outside of the region of interest may experience certain systemic changes as a result of the activation of the axon terminals within the region of interest. As provided herein, preferential activation or direct activation may refer to the cells or structures (e.g., synapses) that experience direct application of energy (e.g., the energy is applied directly to the cells or structures) and are within a region of interest. For example, axon terminals, axoextracellular synapses, and/or postsynaptic non-neuronal cells or interstitial or body fluid within the region of interest may directly experience the applied energy as provided herein. Preferential or direct activation may be considered in contrast to areas outside of a region of interest that do not experience direct energy application, even if such areas nonetheless undergo physiological changes as a result of the energy application.

Neuromodulation is a technique in which energy from an external energy source is applied to certain areas of the nervous system to activate or increase the nerve or nerve function and/or block or decrease the nerve or nerve function. In certain neuromodulation techniques, one or more electrodes are applied at or near target nerves, and the application of energy is carried through the nerve (e.g., as an action potential) to cause a physiological response in areas of the downstream of the energy application site. However, because the nervous system is complex, it is difficult to predict the scope and eventual endpoint of the physiological response for a given energy application site. In one example, stimulation of axon terminals releases neurotransmitter/neuropeptide or induces altered neurotransmitter release in a vicinity of neighboring non-neuronal cells such as secretory or other cells and modulates cell activity of the neighboring or nearby non-neuronal cells, including the postsynaptic cells.

Benefits of the present techniques include local modulation at the region of interest of the tissue to achieve physiological perturbations that may be used to assess a subject condition. Further, the local modulation may involve direct activation of a relatively small region of tissue (e.g., less than 25% of a total tissue volume) to achieve these effects. In this manner, the total applied energy is relatively small to achieve a desired physiological perturbation. In certain embodiments, the applied energy may be from a noninvasive extracorporeal energy source (e.g., ultrasound energy source, mechanical vibrator). For example, a focused energy probe may apply energy through a subject's skin and is focused on a region of interest of an internal tissue. Such embodiments achieve the desired physiological perturbation without invasive procedures or without side effects that may be associated with other types of procedures or therapy.

In certain embodiments, techniques for neuromodulation are provided in which energy from an energy source (e.g., an external or extracorporeal energy source) is applied to axon terminals in a manner such that the induced physiological perturbation, for example, neurotransmitter release, at the site of focus of the energy application, e.g., the axon terminals, is triggered in response to the energy application and not in response to an action potential. That is, the application of energy directly to the axon terminals acts in lieu of an action potential to facilitate neurotransmitter release into a neuronal junction (i.e., synapse) with a non-neuronal cell. The application of energy directly to the axon terminals further induces an altered neurotransmitter release from the axon terminal within the synapse (e.g., axoextracellular synapse) into the vicinity of neighboring non-neuronal cells. In one embodiment, the energy source is an extracorporeal energy source, such as an ultrasound energy source or a mechanical vibrator. In this manner, non-invasive and targeted neuromodulation may be achieved directly at the site of energy focus rather than via stimulation at an upstream site that in turn triggers an action potential to propagate to the downstream site target and to activate downstream targets.

In certain embodiments, the target tissues are internal tissues or organs that are difficult to access using electrical stimulation techniques with electrodes. Contemplated tissue targets include gastrointestinal (GI) tissue (stomach, intestines), muscle tissue (cardiac, smooth and skeletal), epithelial tissue (epidermal, organ/GI lining), connective tissue, glandular tissues (exocrine/endocrine), organ tissue, etc. In one example, focused application of energy at a neuromuscular junction facilitates neurotransmitter release at the neuromuscular junction without an upstream action potential. In one embodiment, contemplated targets or regions of interest for modulation may include portions of a pancreas responsible for controlling insulin release or portions of the liver responsible for glucose regulation. In another embodiment, contemplated regions of interest may be located in the liver. In another embodiment, contemplated regions of interest may be located in the spleen. However, it should be understood that these embodiments are by way of example.

To that end, the disclosed neuromodulation techniques may be used in conjunction with a neuromodulation system. FIG. 1 is a schematic representation of a system 10 for neuromodulation to achieve neurotransmitter release and/or activate components (e.g., the presynaptic cell, the postsynaptic cell) of a synapse in response to an application of energy. The depicted system includes a pulse generator 14 coupled to an energy application device 12 (e.g., an ultrasound transducer). The energy application device 12 is configured to receive energy pulses, e.g., via leads or wireless connection, that in use are directed to a region of interest of an internal tissue or an organ of a subject, which in turn results in a targeted physiological perturbation. In certain embodiments, the pulse generator 14 and/or the energy application device 12 may be implanted at a biocompatible site (e.g., the abdomen), and the lead or leads couple the energy application device 12 and the pulse generator 14 internally. For example, the energy application device 12 may be a MEMS transducer, such as a capacitive micromachined ultrasound transducer.

In certain embodiments, the energy application device 12 and/or the pulse generator 14 may communicate wirelessly, for example with a controller 16 that may in turn provide instructions to the pulse generator 14. In other embodiments, the pulse generator 14 may be an extracorporeal device, e.g., may operate to apply energy transdermally or in a noninvasive manner from a position outside of a subject's body, and may, in certain embodiments, be integrated within the controller 16. In embodiments in which the pulse generator 14 is extracorporeal, the energy application device 12 may be operated by a caregiver and positioned at a spot on or above a subject's skin such that the energy pulses are delivered transdermally to a desired internal tissue. Once positioned to apply energy pulses to the desired site, the system 10 may initiate neuromodulation to achieve targeted physiological perturbation or clinical effects.

In certain embodiments, the system 10 may include an assessment device 20 that is coupled to the controller 16 and that assesses characteristics that are indicative of whether the targeted physiological perturbation of the modulation have been achieved. In one embodiment, the targeted physiological perturbation may be local. For example, the modulation may result in local tissue or function changes, such as tissue structure changes, local change of concentration of certain molecules, tissue displacement, increased fluid movement, etc.

The modulation may result in systemic or non-local changes, and the targeted physiological perturbation may be related to a change in concentration of circulating molecules or a change in a characteristic of a tissue that does not include the region of interest to which energy was directly applied. In one example, tissue displacement may be a proxy measurement for a desired modulation, and displacement measurements below an expected displacement value may result in modification of modulation parameters until an expected displacement value is induced. Accordingly, the assessment device 20 may be configured to assess molecule concentration or activity changes in some embodiments. For example, the assessment device 20 may include a chemical sensor for the molecule of interest. In some embodiments, the assessment device 20 may be an imaging device configured to assess changes in organ size and/or position, fluid flow changes, RNA or protein expression changes, or other indicators of physiological perturbations. In another embodiment, the assessment device 20 may be a circulating glucose monitor and/or a continuous glucose monitor that measures interstitial fluid glucose. The assessment device 20 may be an MRI device or other devices than is capable of acquiring image data of a subject to identify systemic changes. The assessment device 20 may be an ECG or other physiological monitor. While the depicted elements of the system 10 are shown separately, it should be understood that some or all of the elements may be combined with one another. Further, some or all of the elements may communicate in a wired or wireless manner with one another.

Based on the assessment, the modulation parameters of the controller 16 may be altered. For example, if a desired modulation is associated with a change in concentration (circulating concentration or tissue concentration of one or more molecules) within a defined time window (e.g., 5 minutes, 30 minutes after a procedure of energy application starts) or relative to a baseline at the start of a procedure, a change of the modulation parameters such as pulse frequency or other parameters may be desired, which in turn may be provided to the controller 16, either by an operator or via an automatic feedback loop, for defining or adjusting the energy application parameters or modulation parameters of the pulse generator 14.

The system 10 as provided herein may provide energy pulses according to various modulation parameters. For example, the modulation parameters may include various stimulation time patterns, ranging from continuous to intermittent. With intermittent stimulation, energy is delivered for a period of time at a certain frequency during a signal-on time. The signal-on time is followed by a period of time with no energy delivery, referred to as signal-off time. The modulation parameters may also include frequency and duration of a stimulation application. The application frequency may be continuous or delivered at various time periods, for example, within a day or week. In one example, the modulation may be specified relative to a time of day (morning, evening, night) or relative to meals (fasted, non-fasted) The treatment duration to cause the physiological perturbations may last for various time periods, including, but not limited to, from a few minutes to several hours. In certain embodiments, treatment duration with a specified stimulation pattern may last for one hour, repeated at, e.g., 72 hour intervals. In certain embodiments, energy may be delivered at a higher frequency, say every three hours, for shorter durations, for example, 30 minutes. The application of energy, in accordance with modulation parameters, such as the treatment duration and frequency, may be adjustably controlled to achieve a desired result.

Figure 2:
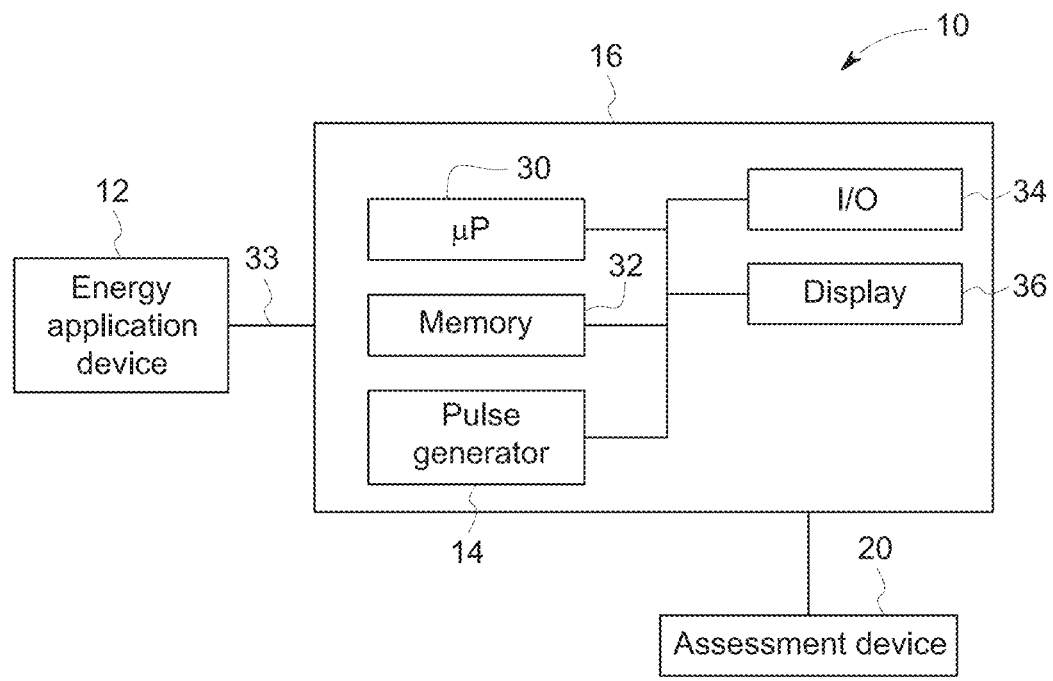
FIG. 2 is a block diagram of a neuromodulation system according to embodiments of the disclosure.

FIG. 2 is a block diagram of certain components of the system 10. As provided herein, the system 10 for neuromodulation may include a pulse generator 14 that is adapted to generate a plurality of energy pulses for application to a tissue of a subject. The pulse generator 14 may be separate or may be integrated into an external device, such as a controller 16. The controller 16 includes a processor 30 for controlling the device. Software code or instructions are stored in memory 32 of the controller 16 for execution by the processor 30 to control the various components of the device. The controller 16 and/or the pulse generator 14 may be connected to the energy application device 12 via one or more leads 33 or wirelessly.

The controller 16 also includes a user interface with input/output circuitry 34 and a display 36 that are adapted to allow a clinician to provide selection inputs or modulation parameters to modulation programs. Each modulation program may include one or more sets of modulation parameters including pulse amplitude, pulse width, pulse frequency, etc. The pulse generator 14 modifies its internal parameters in response to the control signals from controller device 16 to vary the stimulation characteristics of energy pulses transmitted through lead 33 to an subject to which the energy application device 12 is applied. Any suitable type of pulse generating circuitry may be employed, including but not limited to, constant current, constant voltage, multiple-independent current or voltage sources, etc. The energy applied is a function of the current amplitude and pulse width duration. The controller 16 permits adjustably controlling the energy by changing the modulation parameters and/or initiating energy application at certain times or cancelling/suppressing energy application at certain times. In one embodiment, the adjustable control of the energy application device is based on information about a concentration of one or more molecules in the subject (e.g., a circulating molecule). If the information is from the assessment device 20, a feedback loop may drive the adjustable control. For example, a diagnosis may be made based on circulating glucose concentration, as measured by the assessment device 20, in response neuromodulation. When the concentration is above a predetermined threshold or range, the controller 16 may initiate a treatment protocol of energy application to a region of interest (e.g., liver) and with modulation parameters that are associated with a reduction in circulating glucose. The treatment protocol may use different modulation parameters than those used in the diagnosis protocol (e.g., higher energy levels, more frequent application). The controller may initiate a treatment protocol of energy application to a region of interest (e.g. spleen or immune tissue) and with modulation parameters that are associated with an increase or reduction in circulating cytokines or immune cell number, activity, or phenotype.

In one embodiment, the memory 32 stores different operating modes that are selectable by the operator. For example, the stored operating modes may include instructions for executing a set of modulation parameters associated with a particular treatment site, such as regions of interest in the liver, pancreas, gastrointestinal tract, spleen. Different sites may have different associated modulation parameters. Rather than having the operator manually input the modes, the controller 16 may be configured to execute the appropriate instruction based on the selection. In another embodiment, the memory 32 stores operating modes for different types of procedures. For example, activation may be associated with a different stimulating pressure or frequency range relative to those associated with depressing or blocking tissue function. In a specific example, when the energy application device is an ultrasound transducer, the time-averaged power (temporal average intensity) and peak positive pressure are in the range of 1 mW/cm2-30,000 mW/cm2 (temporal average intensity) and 0.1 MPa to 7 MPa (peak pressure). In one example, the temporal average intensity is less than 35 W/cm2 in the region of interest to avoid levels associated with thermal damage & ablation/cavitation. In another specific example, when the energy application device is a mechanical actuator, the amplitude of vibration is in the range of 0.1 to 10 mm. The selected frequencies may depend on the mode of energy application, e.g., ultrasound or mechanical actuator. The controller 16 may be capable of operating in a diagnosis protocol mode and the results of the diagnosis may trigger a change to a treatment operating mode. For example, a diagnosis mode may apply neuromodulating energy once or repeatedly within a relatively short time window (1 hour), while a treatment operating mode may involve repeated neuromodulation events (e.g., daily, hourly) during a treatment protocol.

The system may also include an imaging device that facilitates focusing the energy application device 12. In one embodiment, the imaging device may be integrated with or the same device as the energy application device 12 such that different ultrasound parameters (frequency, aperture, or energy) are applied for selecting (e.g., spatially selecting) a region of interest and for focusing energy to the selected region of interest for targeting and subsequently neuromodulation. In another embodiment, the memory 32 stores one or more targeting or focusing modes that is used to spatially select the region of interest within an organ or tissue structure. Spatial selection may include selecting a subregion of an organ to identify a volume of the organ that corresponds to a region of interest. Spatial selection may rely on image data as provided herein. Based on the spatial selection, the energy application device 12 may be focused on the selected volume corresponding to the region of interest. For example, the energy application device 12 may be configured to first operate in the targeting mode to apply a targeting mode energy that is used to capture image data to be used for identifying the region of interest. The targeting mode energy is not at levels and/or applied with modulation parameters suitable for preferential activation. However, once the region of interest is identified, the controller 16 may then operate in a treatment mode according to the modulation parameters associated with preferential activation.

The controller 16 may also be configured to receive inputs related to the targeted physiological perturbations as an input to the selection of the modulation parameters. For example, when an imaging modality is used to assess a tissue characteristic, the controller 16 may be configured to receive a calculated index or parameter of the characteristic. Based on whether the index or parameter is above or below a predefined threshold, a diagnosis may be made, and an indication of the diagnosis may be provided (e.g., via a display). In one embodiment, the parameter can be a measure of tissue displacement of the affected tissue or a measure of depth of the affected tissue. Other parameters may include assessing a concentration of one or more molecules of interest (e.g., assessing one or more of a change in concentration relative to a threshold or a baseline/control, a rate of change, determining whether concentration is within a desired range). Further, the energy application device 12 (e.g., an ultrasound transducer) may operate under control of the controller 16 to a) acquire image data of a tissue that may be used to spatially select a region of interest within the target tissue b) apply the modulating energy to the region of interest and c) acquire image to determine that the targeted physiological perturbation has occurred (e.g., via displacement measurement). In such an embodiment, the imaging device, the assessment device 20 and the energy application device 12 may be the same device.

Figure 3:
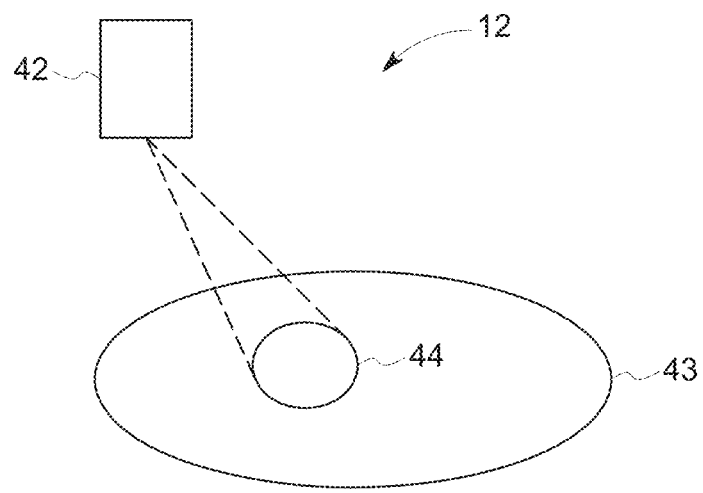
FIG. 3 is a schematic representation of a neuromodulation

FIG. 3 is a specific example in which the energy application device 12 includes an ultrasound transducer 42 that is capable of applying energy to a target tissue 43, e.g., a liver, a spleen, a pancreas. The energy application device 12 may include control circuitry for controlling the ultrasound transducer 42. The control circuitry of the processor 30 (FIG. 2) may be integral to the energy application device 12 (e.g., via an integrated controller 16) or may be a separate component. The ultrasound transducer 42 may also be configured to acquire image data to assist with spatially selecting a desired or targeted region of interest and focusing the applied energy on the region of interest of the target tissue or structure.

The desired target tissue 43 may be an internal tissue or an organ that includes synapses of axon terminals and non-neuronal cells. The synapses may be stimulated by direct application of energy to the axon terminals within a field of focus of the ultrasound transducer 42 focused on a region of interest 44 of the target tissue 43 to cause release of molecules into the synaptic space, e.g., the release of neurotransmitters and/or the change in ion channel activity in turn causes downstream effects. Sensory synapses (or communicating cells) may also be stimulated by direct application of energy to peripheral terminals and neurons within a field of focus of the ultrasound transducer focused on a region of interest of the target tissue and cause direct neural signaling back to the CNS (i.e. driving or mimicking sensory inputs to CNS control centers, ganglia, and nuclei). The region of interest may be selected to include a certain type of axon terminal, such as an axon terminal of a particular neuron type and/or one that forms a synapse with a certain type of non-neuronal cell. Accordingly, the region of interest 44 may be selected to correspond to a portion of the target tissue 43 with the desired axon terminals (and associated non-neuronal cells). The energy application may be selected to preferentially trigger a release of one or more molecules such as neurotransmitters from the nerve within the synapse or directly activate the non-neuronal cell itself through direct energy transduction (i.e. mechanotransduction or voltage-activated proteins within the non-neuronal cells), or cause an activation within both the neural and non-neuronal cells that elicits a desired physiological effect. The region of interest may be selected as the site of nerve entry into the organ. In one embodiment, liver stimulation or modulation may refer to a modulation of the region of interest 44 at or adjacent to the porta hepatis.

The energy may be focused or substantially concentrated on a region of interest 44 and to only part of the internal tissue 43, e.g., less than about 50%, 25%, 10%, or 5% of the total volume of the tissue 43. In one embodiment, energy may be applied to two or more regions of interest 44 in the target tissue 43, and the total volume of the two or more regions of interest 44 may be less than about 90%, 50%, 25%, 10%, or 5% of the total volume of the tissue 43. In one embodiment, the energy is applied to only about 1%-50% of the total volume of the tissue 43, to only about 1%-25% of the total volume of the tissue 43, to only about 1%-10% of the total volume of the tissue 43, or to only about 1%-5% of the total volume of the tissue 43. In certain embodiments, only axon terminals in the region of interest 44 of the target tissue 43 would directly receive the applied energy and release neurotransmitters while the unstimulated axon terminals outside of the region of interest 44 do not receive substantial energy and, therefore, are not activated/stimulated in the same manner. In some embodiments, axon terminals in the portions of the tissue directly receiving the energy would induce an altered neurotransmitter release. In this manner, tissue subregions may be targeted for neuromodulation in a granular manner, e.g., one or more subregions may be selected. In some embodiments, the energy application parameters may be chosen to induce preferential activation of either neural or non-neuronal components within the tissue directly receiving energy to induce a desired combined physiological effect. In certain embodiments, the energy may be focused or concentrated within a volume of less than about 25 mm$^3$. In certain embodiments, the energy may be focused or concentrated within a volume of about 0.5 mm$^3$-50 mm$^3$. A focal volume and a focal depth for focusing or concentrating the energy within the region of interest 44 may be influenced by the size/configuration of the energy application device 12. The focal volume of the energy application may be defined by the field of focus of the energy application device 12.

As provided herein, the energy may be substantially applied only to the region or regions of interest 44 to preferentially activate the synapse in a targeted manner to achieve targeted physiological perturbations and is not substantially applied in a general or a nonspecific manner across the entire tissue 43. Accordingly, only a subset of a plurality of different types of axon terminals in the tissue 43 is exposed to the direct energy application. The disclosed techniques may be used in assessment of subject condition as a result of the perturbations caused by neuromodulation. The disclosed techniques may use direct assessments of tissue condition or function as the targeted physiological perturbations. The techniques may also be used to detect deviation from or toward a homeostatic state or set-point of a physiological neuroimmune, neurohormonal, and/or nerve reflex system. The assessment may occur before (i.e., baseline assessment), during, and/or after the neuromodulation. The assessment techniques may include at least one of functional magnetic resonance imaging, diffusion tensor magnetic resonance imaging, positive emission tomography, acoustic monitoring, thermal monitoring, or chemical sensing (e.g., immunochemical sensing). The assessment techniques may also include protein and/or molecule concentration assessment. The images from the assessment techniques may be received by the system for automatic or manual assessment. Based on the image data, the modulation parameters may also be modified. For example, a change in organ size or displacement may be utilized as a marker of local neurotransmitter concentration, and used as a surrogate marker for exposure of local cells to phenotype modulating neurotransmitters, and effectively as a marker of predicted effect on glucose metabolic pathways. The local concentration may refer to a concentration within a field of focus of the energy application.

Additionally or alternatively, the system may assess the presence or concentration of one or more molecules in the tissue or circulating in the blood. The concentration in the tissue may be referred to as a local concentration or resident concentration. Tissue may be acquired by a fine needle aspirate, and the assessment of the presence or levels of molecules of interest (e.g., metabolic molecules, markers of metabolic pathways, peptide transmitters, catecholamines) may be performed by any suitable technique known to one of ordinary skilled in the art.

In other embodiments, the targeted physiological perturbations may include, but are not limited to, tissue displacement, tissue size changes, a change in concentration of one or more molecules (either local, non-local, or circulating concentration), a change in gene or marker expression, afferent activity, and cell migration, etc. For example, tissue displacement (e.g., liver displacement) may occur as a result of energy application to the tissue. By assessing the tissue displacement (e.g., via imaging), other effects may be estimated. For example, a certain displacement may be characteristic of a particular change in molecule concentration. In one example, a 5% liver displacement may be indicative of or associated with a desired reduction in circulating glucose concentration based on empirical data. In another example, the tissue displacement may be assessed by comparing reference image data (tissue image before application of energy to the tissue) to post-treatment image data (tissue image taken after application of energy to the tissue) to determine a parameter of displacement. The parameter may be a maximum or average displacement value of the tissue. If the parameter of displacement is greater than a threshold displacement, the application of energy may be assessed as being likely to have caused the desired targeted physiological perturbation.

In one example, the present techniques may be used to diagnose a subject with a metabolic disorder. The present techniques may also be used to diagnose and/or treat subjects with disorders of glucose regulation. Accordingly, the present techniques may be used to promote homeostasis of a molecule of interest or to promote a desired circulating concentration or concentration range of one or more molecules of interest (e.g., glucose, insulin, glucagon, or a combination thereof). In one embodiment, the present techniques are used to assess clinical conditions associated with circulating (i.e., blood) glucose levels.

In one embodiment, thresholds of glucose concentration may be used to identify blood glucose levels outside of or in the normal range as part of diagnosis of metabolic dysfunction.

Fasted:
Less than 50 mg/dL (2.8 mmol/L): Insulin Shock
50-70 mg/dL (2.8-3.9 mmol/L): low blood sugar/hypoglycemia
70-110 mg/dL (3.9-6.1 mmol/L): normal
110-125 mg/dL (6.1-6.9 mmol/L): elevated/impaired (pre-diabetic)
125 (7 mmol/L): diabetic
Non-fasted (postprandial approximately 2 hours after meal):
70-140 mg/dL: Normal
140-199 mg/dL (8-11 mmol/L): Elevated or "borderline"/prediabetes
More than 200 mg/dL: (11 mmol/L): Diabetes However, as provided herein, the present techniques permit assessment of perturbations as a result of neuromodulation, even in the absence of fasting or nonfasting glucose information. In this manner, patient noncompliance or misreporting may be eliminated as a confounding factor to assessment of metabolic dysfunction. That is, a subject with an unknown fasting or nonfasting state may be perturbed via neuromodulation into an approximated or pseudofasting state, even if that subject is not fasted, e.g., has recently eaten. As provided herein, an approximated fasting state may refer to a state of a patient after (e.g., within 1-6 hours after, within 30 minutes after) neuromodulating energy is applied to a region of interest, e.g., liver, pancreas, GI, associated with metabolism. Based on the subject's profile or response to neuromodulation, the absence or presence of metabolic dysfunction may be identified.

For example, the above normal glucose ranges may be used as recovery targets to track a time to recovery after changes in glucose levels following a perturbation caused by neuromodulation. In another example, a subject with an elevated fasted glucose level that does not experience a change in glucose levels after neuromodulation is diagnosed with a deficit in insulin production (e.g., a pancreatic disorder). In contrast, if that same subject drops glucose levels significantly (more than an expected amount) after neuromodulation that may indicate a problem in the brain control center (e.g. glucose setpoint). Accordingly, in one embodiment, the response to perturbation permits categorizing subjects based on their particular response profile (e.g., a change in glucose vs. a lack of change in glucose concentration). In one embodiment, the perturbation is induced and the concentration of one or more molecules of interest is assessed. Based on the concentration being above or below a threshold, the subject is categorized in a first category or a second category. Further, their response profile may be categorized relative to their baseline state. A subject with normal glucose levels that experiences no change in glucose following neuromodulation-induced perturbation is categorized differently (e.g., placed in a first category) than a subject with elevated glucose levels that experiences no change in glucose following neuromodulation-induced perturbation (e.g., placed in a second category). Accordingly, a level of change relative to baseline is used to categorize subjects. A change relative to baseline that is less than a predetermined threshold is associated with a first category while a change that is greater than the predetermined threshold is associated with a second category. It should be understood that the disclosed categories may include additional subcategories for a subject.

In another example, the present techniques cause perturbations in both fasted and non-fasted subjects. Accordingly, subjects may prefer to be subject to diagnostic neuromodulation that does not involve dietary changes. In addition, in certain embodiments, the subjects also need not be subject to intravenous administration of pharmacologic agents (e.g., glucose, insulin).

In another example, as provided herein, neuromodulation of lymphatic tissue may result in perturbation of immune activity or function. In certain embodiments, neuromodulation of a lymph node results in local enlargement of the lymph node relative to a contralateral lymph node. The enlargement, or hypertrophy, may be associated with a change in peri-lymphatic vessel muscle cell tone, longer term recruitment and re-organization of lymphatic vessels around the lymph node, and/or molecular changes at key barrier tissues (such as high endothelial venules (HEV) within the lymph node) including alteration of important transport proteins (such as aquaporin (water/liquid transport), or CCL21/CXCL13 secretion (cell chemokines)). The perturbations may result in dramatic shifts in cell densities, cell counts, and the overall lymph node tissue environment, including the enlargement. Further, activation of the lymph node may result in an activation chain that expands or amplifies the local activation to systemically activate the lymphatic system. That is, local stimulation may result in downstream and upstream activation of lymphatic systems. Accordingly, local perturbations may be used to activate a systemic immune response. Additional perturbations may include alteration of lymphatic fluid flow, immune cell trafficking into/out of the lymphatic tissue, alteration of immune cell phenotype or local immune response, and/or antigen trafficking into/out of the lymphatic tissue. Local stimulation may enable tissue or location specific increase in lymphatic fluid or immune cell recruitment. Accordingly, in one embodiment, neuromodulation of lymph tissue and an assessment of perturbations to immune activity (or a lack thereof) may be used to diagnose immune dysfunction or immune disorders.

Figure 4:
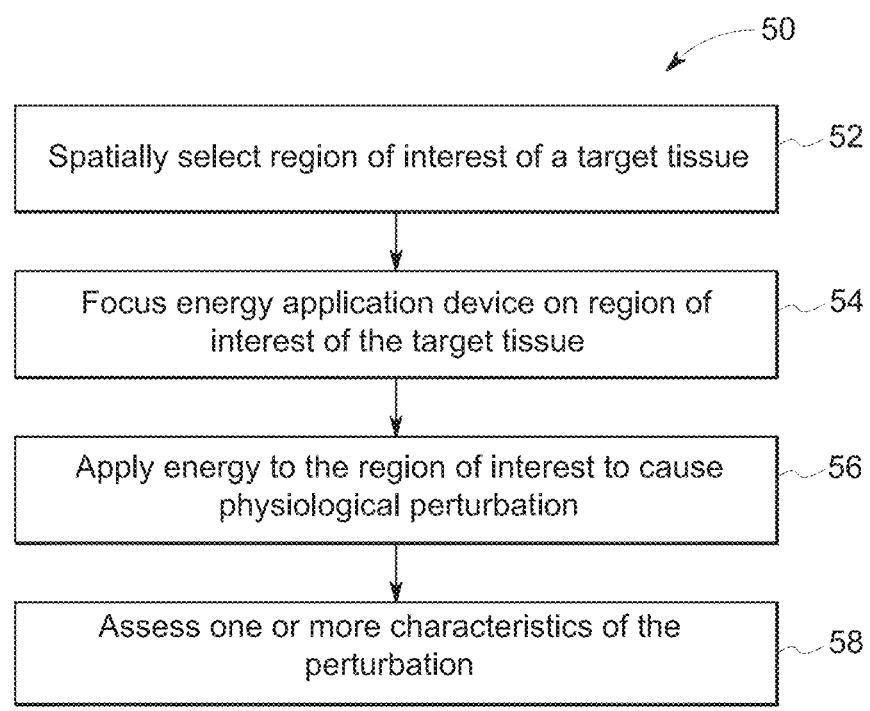
FIG. 4 is a flow diagram of a neuromodulation technique according to embodiments of the disclosure.

FIG. 4 is a flow diagram of a method 50 of causing perturbations via neuromodulation that may be used as part of a diagnosis protocol. In the method 50, the region of interest is spatially selected 52. The energy application device is positioned such that the energy pulses are focused at the desired region of interest at step 54, and the pulse generator applies a plurality of energy pulses to the region of interest of the target tissue at step 56 to preferentially activate a subset of synapses in the target tissue, e.g., to stimulate the axon terminal to release neurotransmitters and/or induce altered neurotransmitter release and/or induce altered activity in the non-neuronal cell (within the synapse) to cause a targeted physiological perturbation at step 58 as provided herein. In certain embodiments, the method may include a step of assessing the effect of the perturbation. For example, one or more direct or indirect assessments of a state of tissue function or condition may be used.

In one embodiment, assessment is performed before and after applying energy pulses to assess a change in glucose concentration as a result of the modulation. Further, the assessed characteristic or condition may be a value or an index, for example, a flow rate, a concentration, a cell population, or any combination thereof, which in turn may be analyzed by a suitable technique. For example, a relative change exceeding a threshold is used to diagnose a subject. The diagnosis is assessed via a measured perturbation, such as a presence or absence of an increase in tissue structure size (e.g., lymph node size) or a change in concentration of one or more released molecules (e.g., relative to the baseline concentration before the neuromodulation). In one embodiment, the perturbation involves an increase in concentration above a threshold, e.g., above a about 50%, 100%, 200%, 400%, 1000% increase in concentration relative to baseline. The assessment involves tracking a decrease in concentration of a molecule over time, e.g., at least a 10%, 20%, 30%, 50%, or 75% decrease in the molecule of interest. Further, for certain subjects, the diagnosis may be associated with a relatively steady concentration of a particular molecule in the context of other clinical events that may tend to increase the concentration of the molecule. That is, a normal subject may respond to glucose administration concurrently with or after neuromodulation in a manner that is distinguishable from an insulin-resistant subject. The increase or decrease or other induced and measurable effect is measured within a certain time window from the start of a treatment, e.g., within about 5 minutes, within about 30 minutes.

Figure 5:
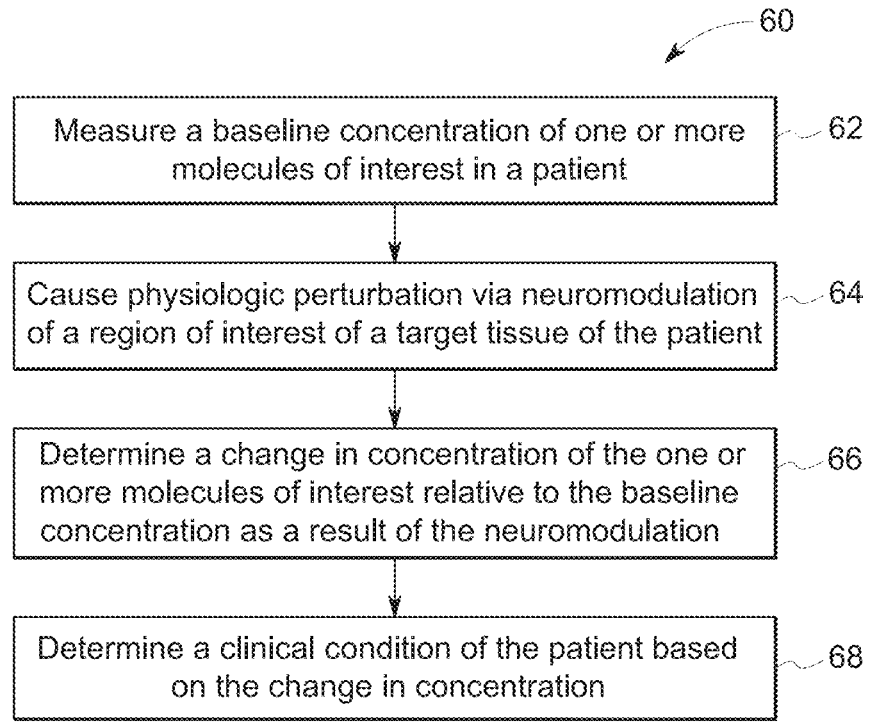
FIG. 5 is a flow diagram of a neuromodulation technique according to embodiments of the disclosure.

FIG. 5 is a flow diagram of a method 60 for assessing perturbations of one or more molecules of interest relative to baseline to diagnose a subject or a part of a diagnosis protocol. For example, the disclosed techniques may be used to categorize subjects as being in a first, second, third, etc. category based on the level of the perturbation response and/or the recovery back towards baseline. The baseline concentration (block 62) may be determined based on the molecule concentration at or before the perturbation and may be a single baseline concentration or an average over several time points before the perturbation. The diagnosis protocol may also include the step of causing physiological perturbations (e.g., as in the method 50 of FIG. 4) via neuromodulation of a region of interest of a target tissue of the subject (block 64). The target tissue may be selected based on the diagnosis protocol. For example, diagnosis of glucose metabolism disorders may involve liver and/or pancreas neuromodulation while diagnosis of immune dysfunction may involve spleen and/or lymph tissue neuromodulation. The region of interest is selected based on the target tissue as disclosed with regard to FIG. 4. Deviation of the concentration of one or more molecules of interest relative to baseline is determined (block 66) at one or more time points. Based on assessment at a time point or a plurality of time points after the application of energy to the region of interest, the subject's clinical condition may be determined (block 68). The time point or time points at which the change in may be determined based on empirical evidence. For example, certain subjects may see changes in the concentration of the molecule of interest by 1, 5, 10, or 60 minutes after neuromodulation. Further, such changes may dissipate towards recovery after a certain period of time (e.g. after 3 hours, 12 hours, 24 hours). Accordingly, the assessment of the change occurs during the time period in which the physiological perturbation is expected to be observed in at least a certain population of subjects or for a certain diagnosis. It should be understood that, in addition, the concentration at additional time points within the recovery period may be assessed. Further, the concentration of the molecule of interest over a period of time may be assessed for predicted increases or decreases (or lack of change) associated with one or more clinical conditions.

The method 60 may be used to diagnose a glucose metabolism disorder. In one embodiment, the present techniques may cause a physiological perturbation that results in an overall decrease in circulating glucose after neuromodulation of the liver (e.g. at a region of interest at or near a porta hepatis), or a change in the concentration or rate of change of glucose relative to circulating hormone concentrations (such as insulin or glucagon). Such changes may be related to the clinical condition of the subject. For example, in diabetic subjects or pre-diabetic subjects, the baseline circulating glucose levels may be at levels greater than 140 mg/dL. After perturbation caused by liver neuromodulation, the perturbed levels of glucose may drop to levels that are consistent with a nondiabetic subject, e.g., levels below 140 mg/dL. Accordingly, a high baseline circulating glucose and a perturbed deviation from the baseline caused by neuromodulation of the liver may be diagnostic of a diabetic or prediabetic subject. In contrast, a normal baseline circulating glucose and no perturbation or a small perturbation of the circulating glucose caused by neuromodulation of the liver may be diagnostic of a healthy or nondiabetic subject. Further, a high baseline circulating glucose and no or a small perturbed deviation from the baseline caused by neuromodulation of the liver may be diagnostic of organ dysfunction, with or without the presence of diabetes. Accordingly, such subjects are considered to be nonresponsive to neuromodulation, and alternate therapy is recommended.

The changes in circulating glucose may be assessed in the context of additional molecules of interest. For example, the relationship between glucose and insulin and resultant perturbations may be indicative of the clinical condition of the subject. In one embodiment, physiological perturbation via targeted liver ultrasound causes observable changes in circulating glucose, insulin, cortisol and triglycerides relative to baseline in diabetic or prediabetic subjects. Perturbations that cause a decrease in glucose without a concurrent change in insulin may be indicative of a first type of glucose metabolism disorder while perturbations that cause a decrease in glucose with a concurrent change in insulin may be indicative of a second type of glucose metabolism disorder. That is, the magnitude of the delta, which may be an observed glucose and/or insulin concentration change (or lack thereof), over time may be a marker of a glucose metabolism disorder. In one example, insulin resistance is characterized by a subject with elevated circulating insulin. In response to neuromodulation of the pancreas according to the present techniques, there is an initial increase in circulating insulin as the mechanical wave likely causes the release of pancreatic insulin stores. However, subsequent to the release of existing pancreatic insulin stores that cause the initial increase, there is a subsequent overall decrease in the circulating insulin relative to both the levels seen in the initial increase as well as relative to the initial or baseline circulating insulin before pancreatic neuromodulation. Observing a response to pancreatic neuromodulation in a subject with elevated circulating insulin and/or elevated circulating glucose above a threshold concurrently with or separate from liver neuromodulation and that tracks the initial increase followed by a decrease in circulating insulin may be used to categorize a subject as insulin resistant without requiring that the subject be fasted. Further, a lack of such a characteristic response may be used to identify subjects that exhibit elevated circulating insulin and/or elevated circulating glucose above a threshold but that are not insulin resistant and that may exhibit such concentrations as a result of other dysfunctional metabolic pathways. Through observing one or more types of perturbations caused by neuromodulation, subjects may be codified or grouped into different categories based on the particular profile of changes. Follow-up diagnosis protocols may track deviation from previous categorization and may, in turn, be used to track subject prognosis.

Lymphatic tissue neuromodulation may be used to perturb populations of immune cells produced by lymphatic structures. In one embodiment, neuromodulation of the lymph nodes may result in an increase in the population of lymphocytes circulating in the lymphatic fluid. Accordingly, the local concentration profile of type 1 (pro-inflammatory) cytokines (e.g. IL-12, TNF-alpha, IFN-gamma, IL-2, TNF-beta) and type 2 (anti-inflammatory) cytokines (e.g. IL-4, IL-10, IL-13, IL-6) may be assessed. In one embodiment, neuromodulation of the lymph nodes may result in an increase or decrease in B or T cells circulating on the lymphatic fluid, or an increase or decrease in B or T cells or dendritic cells recruited into lymphatic tissue. Accordingly, neuromodulation of lymphatic tissue may result in a chance in cell migration patterns. Such migration patterns may be observed using in vivo bioluminescence imaging. Other characteristics may include a change in lymph drainage patterns. In certain embodiments, these changes may be characteristics of the perturbation used to diagnose a subject. Healthy subjects, immunocompromised or immunodeficient subjects, and subjects with a hyperactive immune response may experience different perturbations as a result of neuromodulation of lymph tissue. Characteristics of these perturbations may be assessed to create profiles. A subject with an unknown clinical condition may be diagnosed according to a closest match to a characteristic profile. For example, an immunodeficient subject may have a characteristic lack of response or a low level of perturbations in response to targeted splenic neuromodulation. In certain embodiments, the occipital, auricular, cervical, axillary, inguinal, pulmonary, mediastinal, intraabdominal, or epitrochlear lymph nodes may be targeted.

Figure 6:
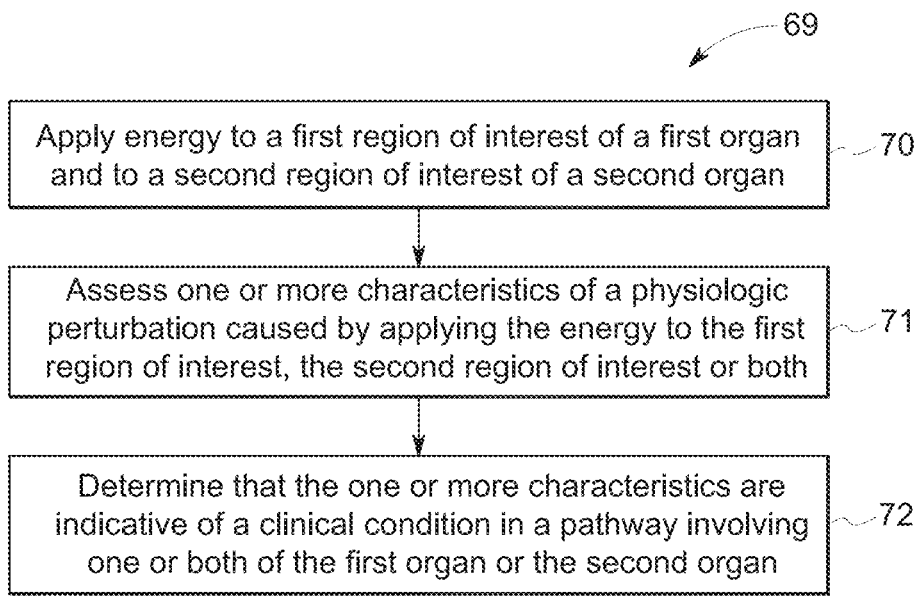
FIG. 6 is a flow diagram of a neuromodulation technique according to embodiments of the disclosure.

FIG. 6 is a method 69 of identifying individual portions of a disordered metabolic pathway based on perturbation patterns. Energy may be applied to individual regions of interest (e.g., a first region of interest, a second region of interest) in different organs (e.g., a first organ, a second organ) to induce neuromodulation and resultant perturbations (block 70). The energy application may be in series (e.g., at different times) to permit assessment of the characteristics of the perturbation at each organ (block 71). The characteristic of the perturbation include measurable physiological changes that are assessed. Based on the assessment, a clinical condition may be diagnosed (block 72). For example, energy may be applied to a liver and a pancreas at different time points to identify point of dysfunction in glucose metabolism. A subject with a diseased pancreas may respond differently than a subject who is insulin resistant. That is, an insulin resistant subject may respond with increased levels of circulating insulin as a result of targeted pancreatic stimulation. However, a subject with a diseased pancreas may be incapable of generating insulin and, therefore, may not exhibit the characteristic of increased circulating insulin as a result of neuromodulation of the pancreas. An insulin-resistant patient may also respond with a decrease in blood glucose that does not coincide with an increase in insulin concentration after stimulation of peripheral sensory sites (such as the liver or GI tract), as stimulation of these sites acts on other CNS based sensory sites that are deficit in glucose sensor and control. Other techniques may not distinguish between these scenarios.

Figure 7:
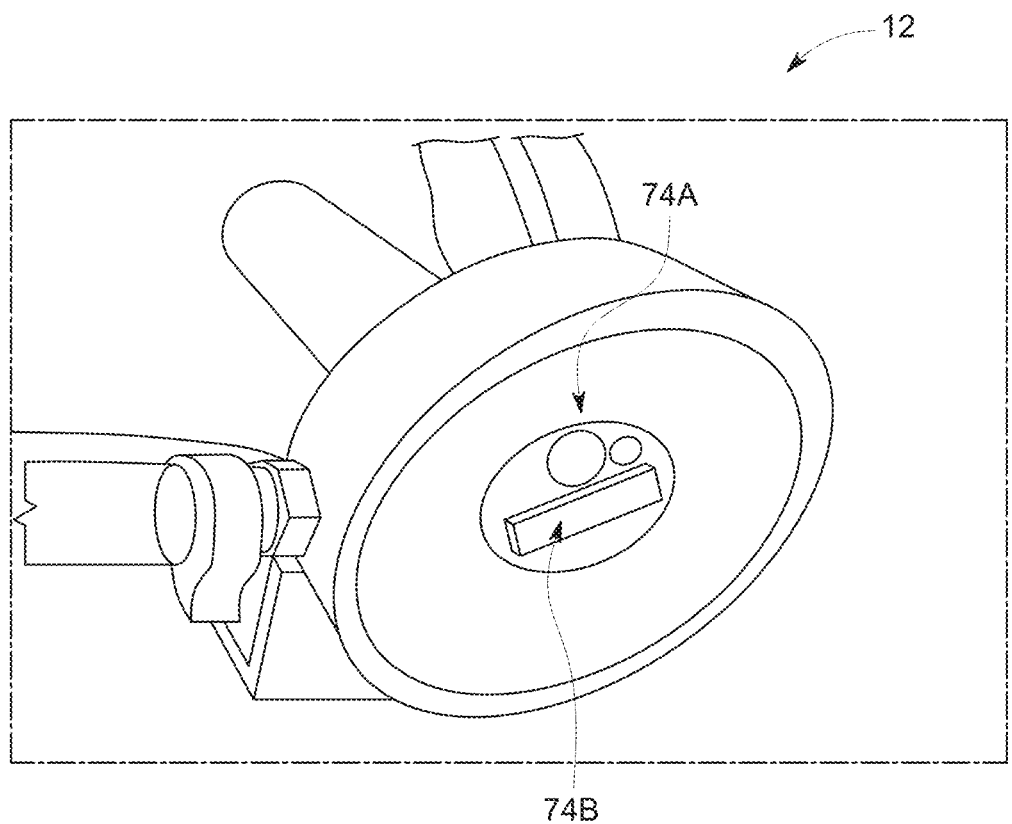
FIG. 7 is a schematic representation of an ultrasound energy application device in operation according to embodiments of the disclosure.
Figure 8:
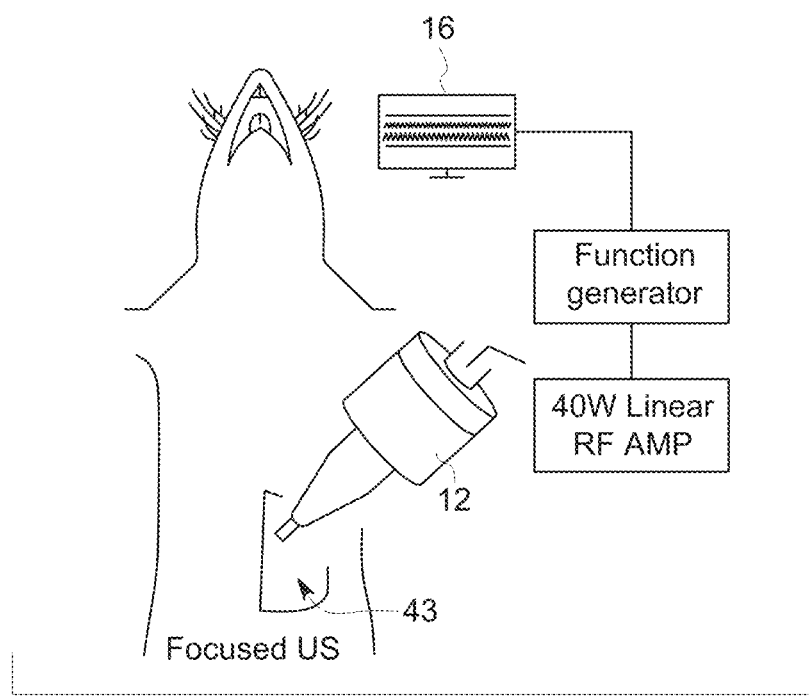
FIG. 8 is a schematic illustration of the experimental setup for ultrasound energy application to achieve targeted physiological perturbations according to embodiments of the disclosure.

The energy application device 12 may be configured as an extracorporeal non-invasive device or an internal device, e.g., a minimally invasive device. As noted, the energy application device 12 may be an extracorporeal noninvasive ultrasound transducer or mechanical actuator. For example, FIG. 7 shows an embodiment of the energy application device 12 configured as a handheld ultrasound probe including an ultrasound transducer 74. However, it should be understood that other noninvasive implementations are also contemplated, including other methods to configure, adhere, or place ultrasound transducer probes over an anatomical target. Further, in addition to handheld configurations, the energy application device 12 may include steering mechanisms responsive to instructions from the controller 16. The steering mechanisms may orient or direct the energy application device 12 towards the target tissue 43 (or structure), and the controller 16 may then focus the energy application onto the region of interest 44. The ultrasound transducer 74 may include an imaging transducer 74A used for spatial selection of the region of interest 44 within the target tissue 43. The ultrasound transducer 74 may include a treatment transducer 74B that applies the neuromodulation energy.

In some embodiments, an ultrasound image may be used to guide the ultrasound stimulus to spatially select a region of interest for targeted delivery of ultrasound stimulus. As provided herein, spatial selection or spatially selecting may include obtaining an image of a tissue or organ (or a portion of a tissue or organ) and, based on image (e.g., the ultrasound image), identifying a region of interest within the organ. In some embodiments, the tissue or organ may have anatomical features that are used to guide the selection of the region of interest within the organ. Such features may, in some embodiments, include a site of blood vessel or nerve entry into an organ, a tissue type within an organ, an interior or edge of an organ, or a suborgan structure, by way of non-limiting example. In certain embodiments, the anatomical feature may include a liver porta hepatis, suborgans of a gastrointestinal tract (stomach, small intestines, large intestines), a pancreatic duct, or a splenic white pulp. By identifying the anatomical features in the image, the region of interest may be selected to overlap with or include the anatomical feature or be adjacent to the anatomical feature. In other embodiments, the anatomical feature may be excluded from the region of interest. For example, an intestinal tissue may be selected as a region of interest rather than a stomach tissue. The identification of the anatomical feature may be via morphological features that are visible in the image (e.g., visible in the ultrasound image) or by structure recognition features of the imaging modality used to obtain the image. As disclosed herein, the system 10 may be configured such that the energy application device 12 is configured to operate in an imaging mode to obtain the image and to subsequently operate in energy application mode after the image is obtained and the region of interest is spatially selected based on the image.

In other embodiments, the region of interest may be identified by the presence or absence of one or more biological markers. Such markers may be assessed by staining the organ or tissue and obtaining images indicative of the stain to identify regions of the organ or tissue that include the biological marker/s. In some embodiments, the biological marker information may be obtained by in vivo staining technologies to obtain location data of the biological marker/s in the tissue or organ specific for the subject in real time. In other embodiments, the biological marker information may be obtained by in vitro staining technologies to obtain location data for one or more representative images that is then used to predict the locations of the biological marker/s within the subject's tissue or organ. In some embodiments, the region of interest is selected to correspond with portion of the tissue or organ that are rich in a particular biological marker or that lack a particular biological marker. For example, the one or more biological markers may include markers for neuronal structures (e.g., myelin sheath markers).

The region of interest in the organ or tissue may be spatially selected based on operator input. For example, an operator may designate the region of interest on the obtained image by directly manipulating the image (i.e., drawing or writing the region of interest on the image) or by providing image coordinate information that corresponds to the region of interest. In another embodiment, the region of interest may be automatically selected based on the image data to achieve spatial selection. In some embodiments, the spatial selection includes storing data related to the region of interest in a memory and accessing the data.

Once spatially selected, the system 10 is configured to apply energy to the region of interest as provided herein.

EXAMPLES

Targeted Physiological perturbations

A GE Vivid E9 ultrasound system and an 11 L probe were used for the ultrasound scan before neuromodulation started. A focal area corresponding to an interior region of interest was labeled on animal skin. The HIFU transducer was positioned on the labeled area. Another ultrasound scan was also performed using a smaller imaging probe (3S), which was placed in the opening of the HIFU transducer. The imaging beam of the 3S probe was aligned with the HIFU beam. Therefore, one could confirm that the HIFU beam was targeted at the region of interest using an image of the targeted organ (visualized on the ultrasound scanner).

Animal Protocols

Adult male obese Zucker rats, 8 to 12 weeks old (250-300 g; Charles River Laboratories), in accordance with conditions maintained at the supplier to promote development of insulin resistance and hyperglycemia. The rats were fed a high fat diet. Neuromodulation using applied ultrasound energy was performed on the liver. The ultrasound application was performed for 1 minute. Blood samples were collected 15 minutes after the last ultrasound treatment to analyze changes in circulating catecholamine concentration (e.g., norepinephrine and dopamine). Terminal blood samples were collected 60-90 minutes after the last ultrasound treatment to analyze changes in circulating molecule concentration. Blood samples were stored with the anticoagulant (disodium) EDTA to prevent coagulation of samples.

The protocol used for ultrasound neuromodulation may be as follows:
(A) Animals may be anesthetized with 2-4% isoflurane.
(B) The animals may be laid prone on a water circulating warming pad to prevent hyperthermia during the procedure.
(C) The region above the targeted region of interest for ultrasound stimulus (e.g., nerve of interest) may be shaved with a disposable razor and animal clippers prior to stimulation.
(D) Diagnostic imaging ultrasound may be used to spatially select the region of interest.
(E) The area may be marked with a permanent marker for later identification.
(F) Either an FUS ultrasound probe or a LogiQ E9 probe may be placed at the designated region of interest previously identified by the diagnostic imaging ultrasound.
(G) An ultrasound pulse may then be performed with a total duration of a single stimulus not surpassing a single 1-minute pulse. Energies of the ultrasound pulses would not reach levels associated with thermal damage and ablation or cavitation (e.g., 35 W/cm$^2$).
(H) A second 1-minute ultrasound pulse may be applied.
(I) The animal may then be allowed to incubate under anesthesia for acute study (e.g., 1 hour) and kinetic study. After which the animal is sacked and tissue and blood samples are collected.

An incision may be made starting at the base of the peritoneal cavity extending up and through to the pleural cavity.

Organs may be rapidly removed and homogenized in a solution of PBS, containing phosphatase (0.2 mM phenylmethylsulfonyl fluoride, 5 µg/mL of aprotinin, 1 mM benzamidine, 1 mM sodium orthovandate and 2 µM canthariddin) and protease (1 µL to 20 mg of tissue as per Roche Diagnostics) inhibitors. A targeted final concentration of 0.2 g tissue per mL PBS solution was applied in all samples. Blood samples were stored with the anti-coagulant (disodium) EDTA to prevent coagulation of samples. Samples are then stored at −80° C. until analysis.

Target Tissue Stimulation and Physiological Perturbation for Diagnosis of Glucose Metabolic Disorders The present examples demonstrate a noninvasive method to achieve physiological perturbation to assess a metabolic dysfunction in a patient. The disclosed techniques provide advantages relative to techniques for assessing metabolic dysfunction that involve hours of patient time, including fasting, infusion, and follow-on response/blood draw steps. For example, in assessment of insulin resistance in a patient according to certain procedures, the patient may undergo a fasting period, which permits the patient's physiological system to achieve a setpoint with respect to a population. After fasting, the patient may be administered glucose or a metabolic active compound (e.g., orally or injected). The patient's response is then measured over a period of time, often hours, by monitoring a change in blood glucose and/or insulin or other hormone that supports changes in the blood glucose concentration. If either fasting glucose or insulin is determined to be above a range (determine by measuring previous population of subjects) then a subject may be diagnosed with diabetes. A Glucose Tolerance Test measures how fast a bolus of glucose is cleared from blood in a fasting state (compared to a population of subjects) and is used to diagnose diabetes in subjects with higher (but not pathologically high) fasting glucose concentrations. Clamp techniques are used to quantify how a subject metabolizes glucose. Clamps may include a hyperglycemic clamp (continuous infusion of glucose; quantify capacity for insulin secretion) or hyper-insulemic clamp (continuous infusion of insulin; quantify insulin resistance) which bring issues relating to cost of assessment, and over complexity affects use in the clinic.

The HOMA (Homeostatic Model Assessment) Calculator uses a mathematical model to estimate insulin sensitivity and B-cell function from plasma insulin and glucose concentrations. This interaction between glucose and insulin in the basal state provides information relating to the balance between hepatic glucose output and insulin secretion, which is maintained by a feedback loop maintained by the liver and B-cells of the pancreas, allowing for HOMA to serve as a surrogate measure of steady state beta cell function (% B) and insulin sensitivity (% S), as percentages of a normal reference population. The predictions used in the model arise from experimental data in humans and animals.

Figure 9:
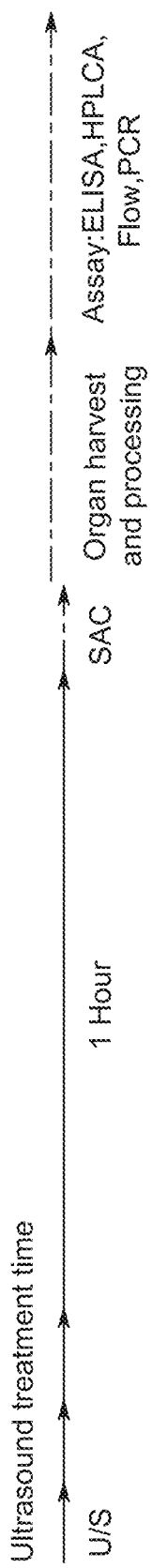
FIG. 9 is an experimental timeline of ultrasound energy application according to embodiments of the disclosure.
Figure 10:
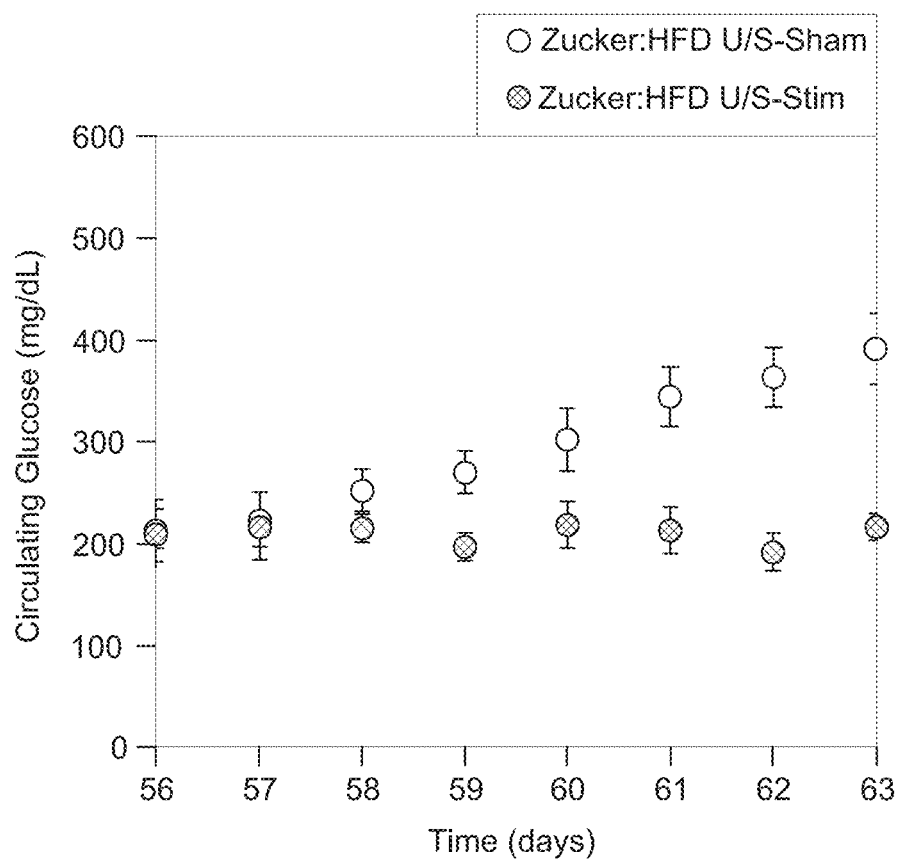
FIG. 10 shows the circulating glucose concentration after ultrasound energy application in a Zucker-HFD animal type 2 diabetes model according to embodiments of the disclosure.
Figure 11:
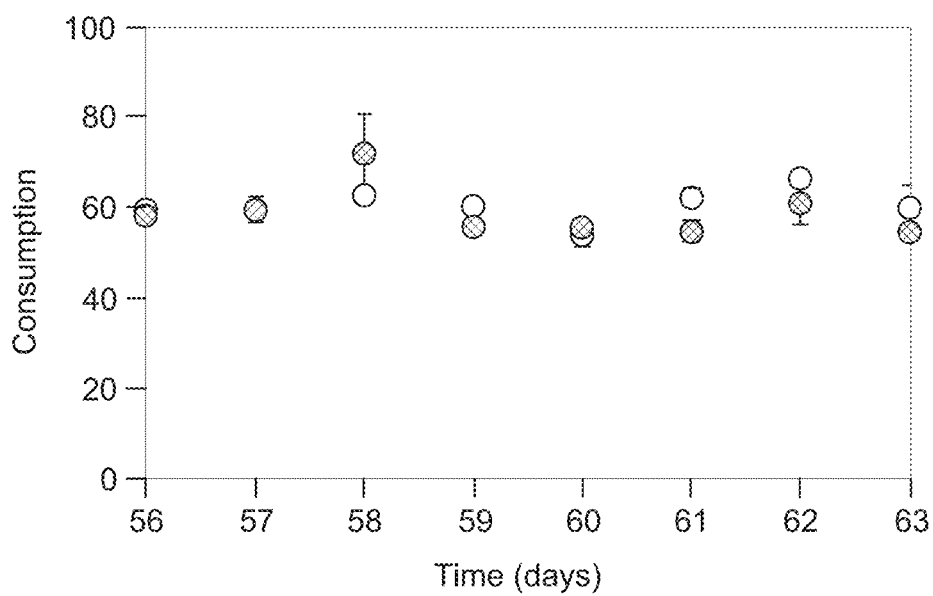
FIG. 11 shows food consumption in the animals during the experimental timeline of FIG. 10.
Figure 12:
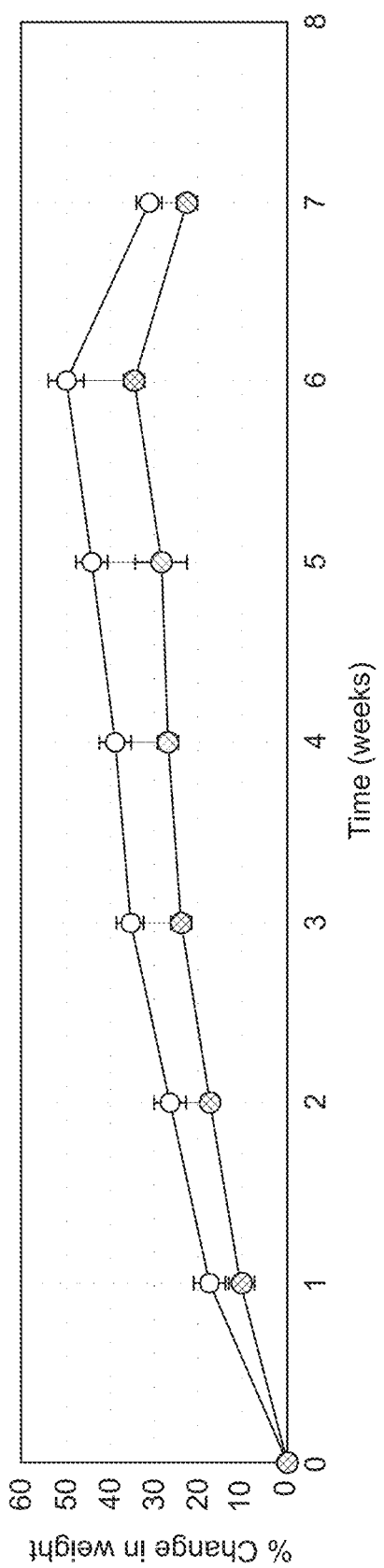
FIG. 12 shows a change in rate of body weight gain in treated vs. control animals in the animals during the experimental timeline of FIG. 10.

The disclosed techniques may replace or be used in conjunction with other techniques for diagnosis of glucose metabolic disorders to eliminate or shorten fasting and follow-on assessment times. In one embodiment, a modified HOMA calculator may be based on the disclosed neuromodulation-induced perturbations to more closely approximate the fasted state of a diabetic subject. That is, rather than requiring a subject to fast for a certain number of hours, a subject (e.g., diabetic, normal, or unknown) may be perturbed via neuromodulation to lower circulating glucose into a state resembling a fasting state for the purposes of assessing glucose response. Moreover, neuromodulation induces a stabilization of glucose levels independent of the feeding state, as indicated by the lack of fluctuation in glucose levels. Taken together, this neuromodulation induced stabilization of glucose reduces the potential confounding results derived from feeding state assessments and permits an assessment of insulin sensitivity in the absence of feeding-derived effects Ultrasound stimulation was performed as provided herein and according to the timeline shown in FIG. 9 to show induced targeted physiological perturbations relative to a control. FIG. 10 shows the results of ultrasound stimulation of the liver (porta hepatis) in obese Zucker rats relative to control rats that underwent sham ultrasound treatment. The ultrasound-treated rats were protected from the increase in circulating glucose in the control rats, even as both groups of rats were housed in conditions associated with the development of insulin resistance and hyperglycemia. Accordingly, the results demonstrate that ultrasound treatment causes perturbations in hyperglycemic rat populations that are detectable via changes in circulating glucose. FIGS. 11 and 12 show feed consumption and weight were similar between the treatment and control groups. The weight gain in the treated animals was slowed relative to the control group (FIG. 12) over the experimental timeline while the feed consumption remained steady (FIG. 11).

Figure 13:
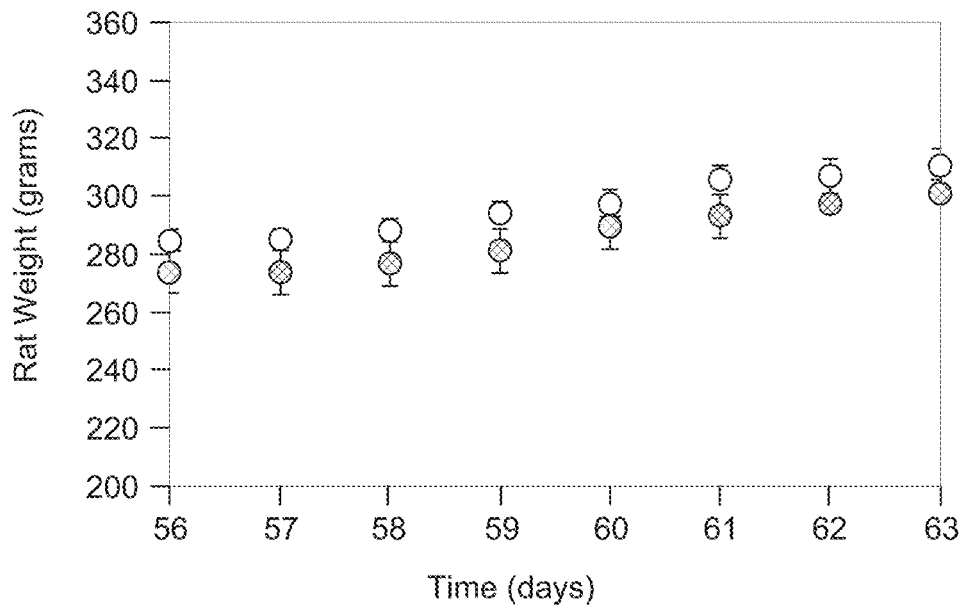
FIG. 13 shows modified Homeostatic Model Assessment of Insulin Resistance scores using a model based on neuromodulation technique according to embodiments of the disclosure in the animals during the experimental timeline of FIG. 10.

As provided herein, liver neuromodulation causes alteration to glucose metabolism to provide a controlled/precise stimulus and modify the relationship between organs to influence or change a current clinical score of homeostasis (i.e. HOMA score), as shown in FIG. 13. The disclosed techniques may be used to generate an index reflective of neuromodulation and resultant perturbations. Typically, the HOMA score is indicative of a relationship between fasting glucose and fasting insulin measures. Generally, higher HOMA scores are reflective of elevated levels of insulin required for glucose disposal. As provided herein, changes in insulin and glucose concentration may be assessed in response to liver neuromodulation as part of a diagnostic protocol to derive a homeostasis index that may be used to diagnose and track insulin resistance, even in subjects with glucose levels in a normal range or not undergoing a controlled diet regimen.

The HOMA model for steady-state is based on circulating glucose and insulin levels through a population-based formula. The assumption is the subject is fasted. Further, the typical assessment is based on "stimulated" responses such as the glucose clamp, insulin clamp or glucose tolerance test. In certain embodiments, neuromodulation replaces the typical fasting and stimulation (e.g., glucose clamp, insulin clamp, glucose tolerance). In one embodiment, the present techniques may be used to replace the glucose and/or insulin infusion with neuromodulation such that the test may be performed without administration of glucose and/or insulin. However, it should be understood that neuromodulation followed by administration of glucose and/or insulin is also contemplated. In another embodiment, the present techniques may be used to eliminate fasting from measurement protocols (by using neuromodulation) to provide immediate deviation from baseline organ kinetics/interactions.

As provided herein, the present techniques may be used to build a population-based model of a relationship between changes in glucose and insulin concentration responses to neuromodulation. The model may be based on glucose-insulin relationships for a population of healthy individuals perturbed to an approximated fasting state via neuromodulation. In certain embodiments, the model may be further based on glucose-insulin relationships for a population of individuals with various types of metabolic function perturbed to an approximated fasting state via neuromodulation. The model may applied to glucose concentration and insulin concentration data acquired from a neuromodulated subject perturbed into an approximated fasting state to generate a score, whereby the score is indicative of a level of insulin resistance in the subject.

Figure 14:
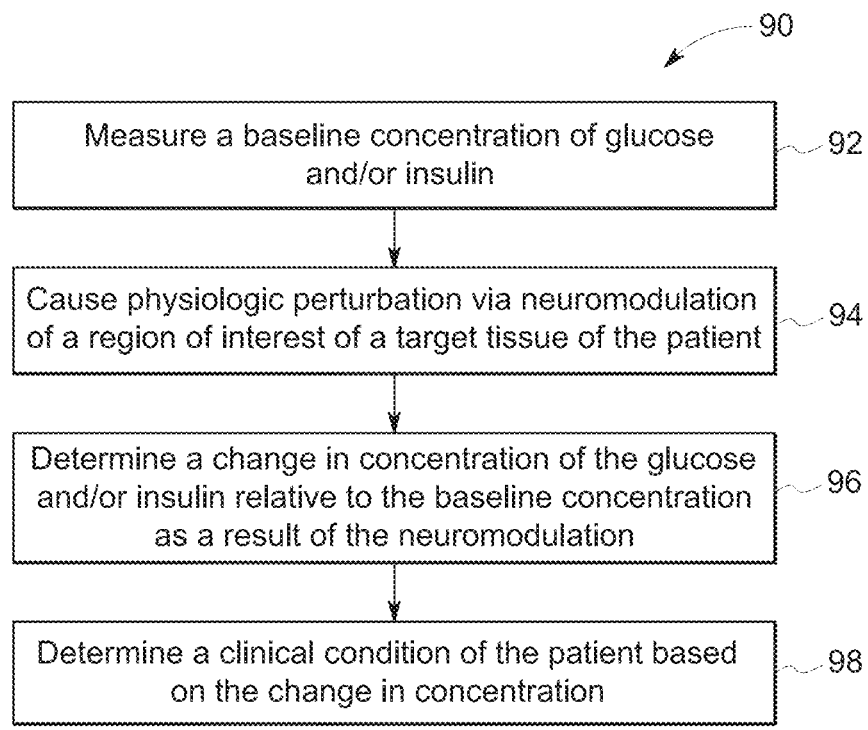
FIG. 14 is a flow diagram of a neuromodulation technique according to embodiments of the disclosure.

In one embodiment, the FIG. 14 is a flow diagram of a method 90 showing a metabolic dysfunction assessment technique. The technique acquires a baseline concentration of glucose and/or insulin at step 92, which may be at a time point immediately before (within 1-6 hours before) or concurrently with initiation of neuromodulation of a region of interest in a target tissue (e.g., liver, GI, pancreas) at step 94. As noted herein, the subject may be monitored using a continuous glucose monitor such that glucose concentrations are available on an ongoing basis. Based on the observed perturbation, which may be reflected in observing changes in glucose and/or insulin concentrations overtime as a result of the neuromodulation at step 96, the clinical condition of the patient may be determined at step 98.

The present techniques may be used to codify subject populations based on level of glucose and/or insulin changes after stimulation or to diagnose type of diabetes and/or level of resistance. For example, subjects may be categorized as "responders" or "strong responders" or "low responders" or "nonresponders" depending on the level of glucose and/or insulin changes. For example, a nonresponder may exhibit a change in concentration that is less than a predetermined threshold relative to a baseline concentration while a responder experiences a change in concentration that is greater than the predetermined threshold. In one example, a nonresponder is considered to exhibit a change in glucose of less than about 5%, less than about 10%, or less than about 15% relative to baseline. A responder is considered to exhibit a change in glucose of greater than about 10-15% relative to baseline, while a strong responder is considered to exhibit a change in glucose of greater than about 50% relative to baseline. The responsiveness may be at a time point associated with an expected change in a healthy or responsive population.

Figure 15:
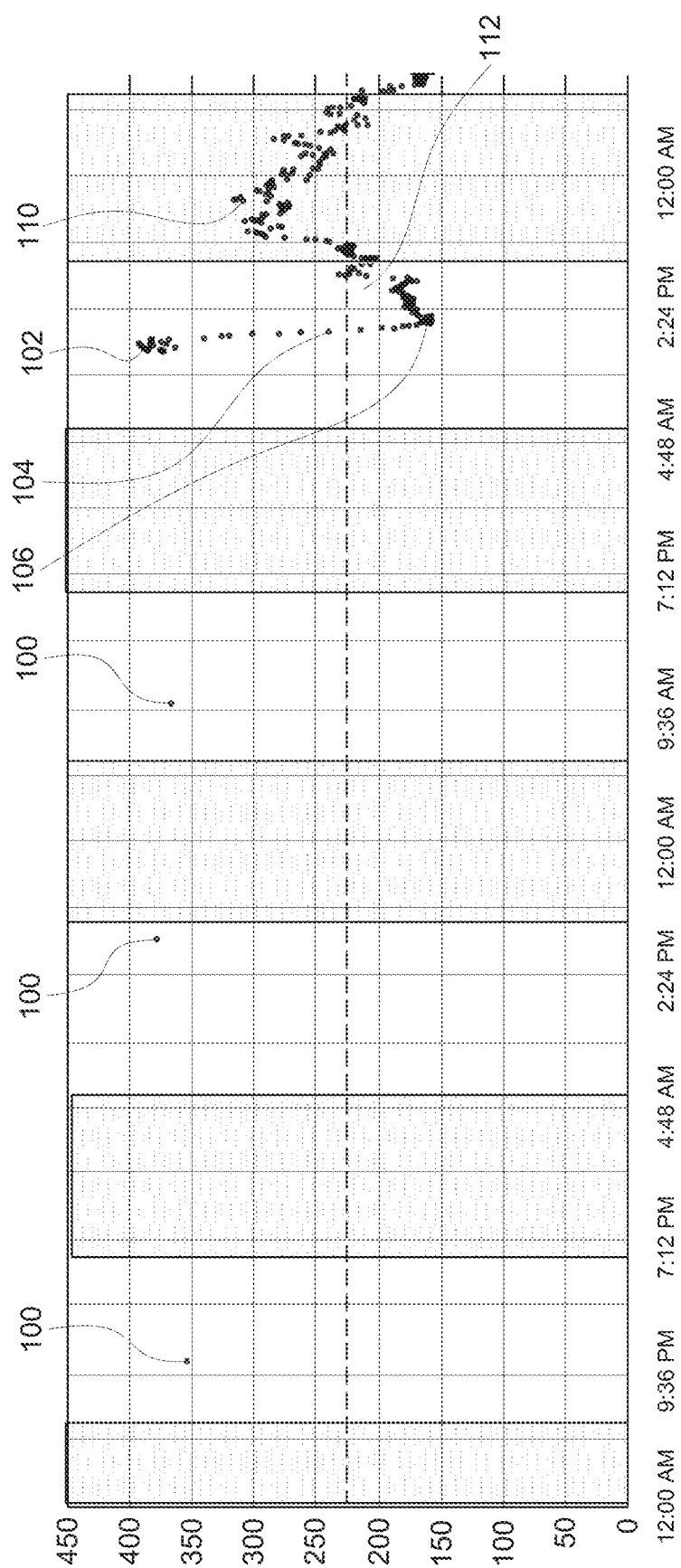
FIG. 15 shows a profile of a response and recovery to a neuromodulation perturbation according to embodiments of the disclosure in a highly insulin resistant subject.

FIG. 15 is an example of a neuromodulation response profile for a highly insulin-resistant animal subject given a diet that drives insulin resistance and high glucose levels. The profile shows glucose concentrations 100 over a time period of several days before initiation of neuromodulation, showing relatively stable and high glucose concentrations above a threshold, shown as glucose concentration of 225 mg/dL. Neuromodulation is initiated at baseline 102, and the glucose response to neuromodulation is tracked over time. The depicted subject is characterized by a steep glucose decrease of long duration and magnitude and without any fasting or glucose administration. As provided herein, the response profile may be assessed or characterized by one or more measures of response. In one embodiment, a magnitude of a change from a peak baseline concentration 102 to a trough 106 may be assessed. Alternatively or additionally, the slope 104 may be assessed (e.g., a steep slope may be indicative of insulin resistance). Additional metrics may include a slope from a trough 106 to a recovery peak 110, a difference between a baseline concentration and a first recovery peak 110, a time to the first recovery peak 101, and/or an area under the curve 112 relative to a setpoint. For example, an insulin-resistant subject may have a relatively short time period of lower glucose concentrations below a predetermined threshold (e.g., lower than 225 mg/dL, lower than 200 mg/dL) before recovery to concentrations above the predetermined threshold, which is reflected in the area under the curve 112 being below an empirically-determined threshold. The subject may be monitored during normal activities, such as eating and sleeping, and the characteristic profile may be reflective of changes in response to these activities relative to baseline. While previous techniques may have involved complex glucose administration response tracking over several hours in additional to pre-test fasting, the present techniques permit observation of changes over a relatively short period of time, which is less of a burden on the tested subject. Accordingly, in one embodiment, the subject is assessed using glucose concentration changes that are observed within 12 hours, 6 hours, 5 hours, 4 hours, 3 hours, two hours, or within one hour after neuromodulation to achieve an approximated fasting state in the subject. Further, because glucose monitoring may be accomplished using glucose monitors that permit subjects to be ambulatory and outside of a clinical setting, the present techniques provide a more convenient and faster assessment of metabolic dysfunction that does not require fasting or administration of a glucose bolus.

Figure 16:
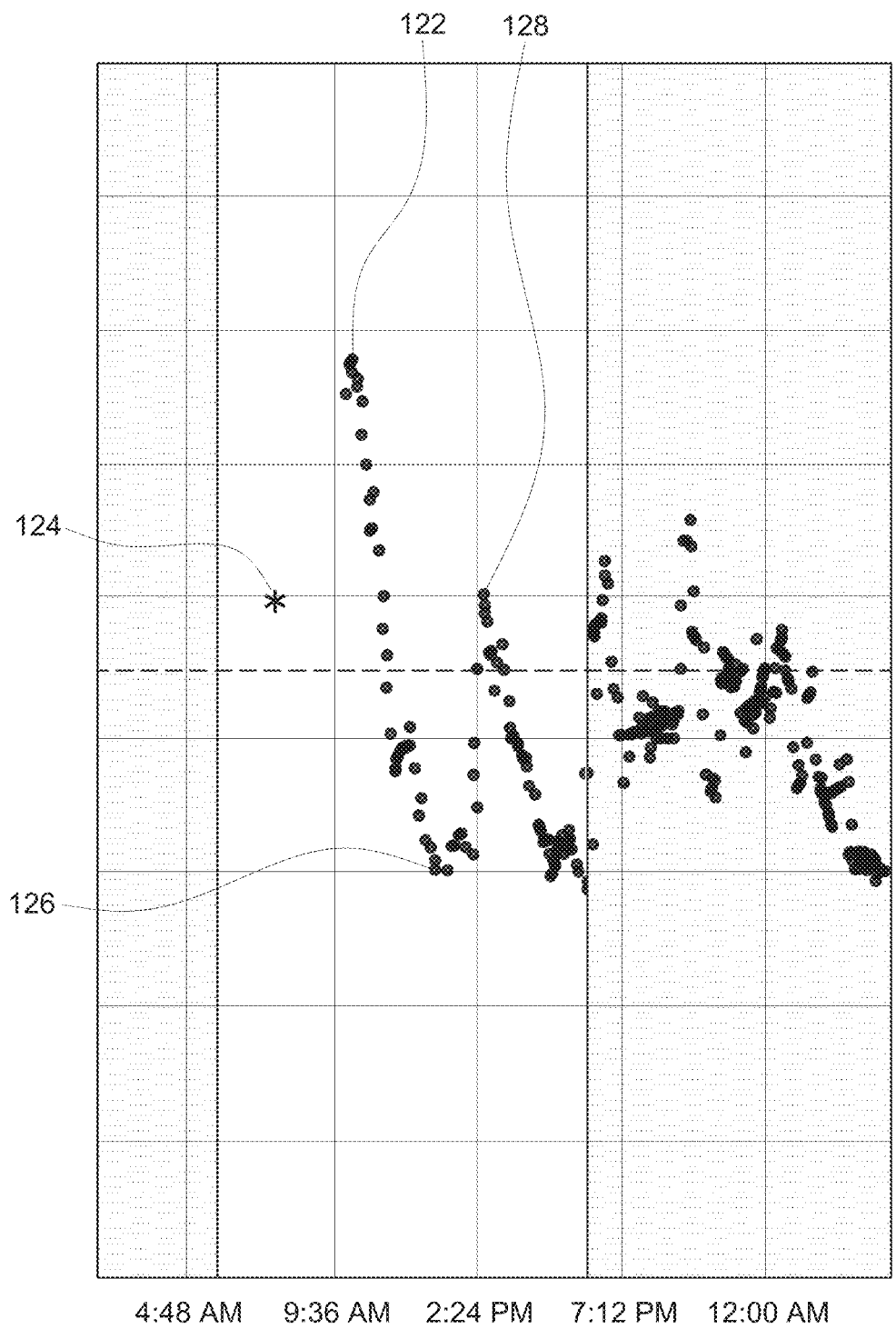
FIG. 16 shows a profile of a response and recovery to a neuromodulation perturbation according to embodiments of the disclosure in a less insulin resistant subject.
Figure 17:
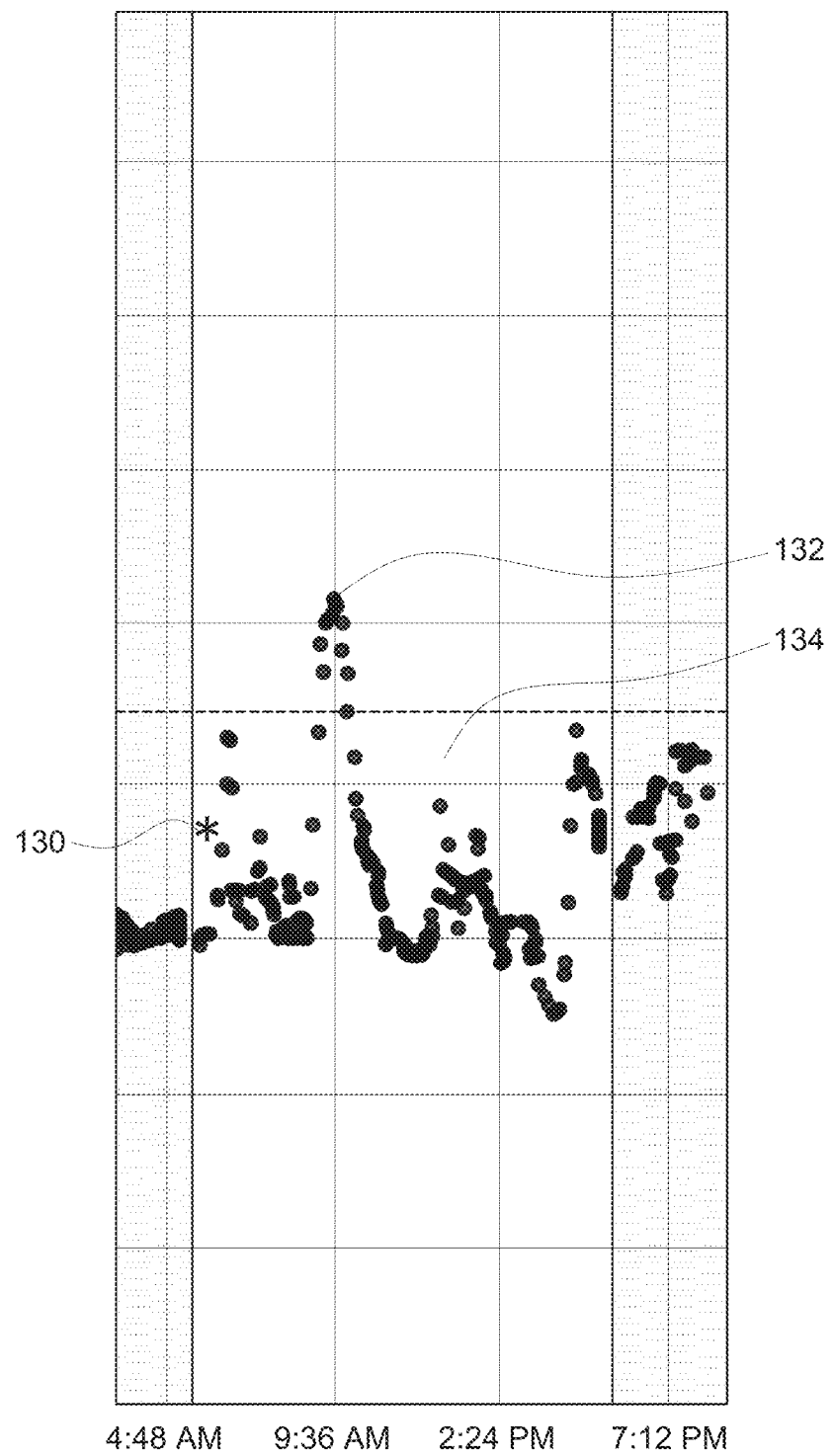
FIG. 17 shows a profile of a response and recovery to a neuromodulation perturbation according to embodiments of the disclosure in a less insulin resistant subject.

FIG. 16 is an example of a neuromodulation response profile for an insulin-resistant subject with a starting glucose concentration that is lower than that of the subject of FIG. 15. The profile shows a pre-treatment glucose concentration 124 above a threshold (e.g., approximately 250 mg/dL) and a higher baseline concentration 122 that is lowered to a trough 126 in response to neuromodulation and a recovery peak 128 or an area under the curve 112 relative to a setpoint. For example, an insulin-resistant subject may have a relatively short time period of lower glucose concentrations below a predetermined threshold (e.g., lower than 225 mg/dL, lower than 200 mg/dL) before recovery to concentrations above the predetermined threshold. The response profile is of lower magnitude and duration while nonetheless showing a steep decrease in glucose concentrations. Accordingly, in certain embodiments, a response profile as in FIG. 15 and as in FIG. 16 may both be classified as being insulin resistant, although in different bands or categories. FIG. 17 is a response profile of a subject with a starting glucose concentration 130 below diabetic levels and that shows little or no response to neuromodulation. Accordingly, the subject may be considered to be a nonresponder and may be classified differently relative to the profiles in FIG. 15 and FIG. 16.

In another embodiment, the disclosed techniques may be used for detection of differences in subject populations for a variety of perturbations and their associated clinical conditions, and/or optimal therapeutic regimen. The subject population differences may result in categorizing the subjects into one of several categories and initiating treatment options based on the categorization. For example, drug response may be correlated to a responsiveness (e.g., a degree of perturbation) to neuromodulation. Further, the disclosed techniques may provide category information (insulin resistant, not insulin resistant, responder, nonresponder) as well as additional data as part of a report to a caregiver.

Target Tissue Stimulation and Physiological Perturbation for Identification of Pathogen or Toxin Exposure As provided herein, a neuromodulation response may be indicative of pathogen, toxin, or environmental exposure prior to the time-point where either the pathogen itself is detectable or disease symptoms manifest (i.e. fever, etc). That is, the present techniques provide an improved and more rapid assessment of pathogen exposure. Such assessments may improve outcomes for hospital-associated pathogens that, when detected more rapidly, may be more effectively contained. While certain techniques that track immune or systemic responses require continuous monitoring to detect exposure to a pathogen, the present techniques eliminate the requirement for baseline monitoring by comparing changes before and after neuromodulation in the expression of certain markers.

Figure 18:
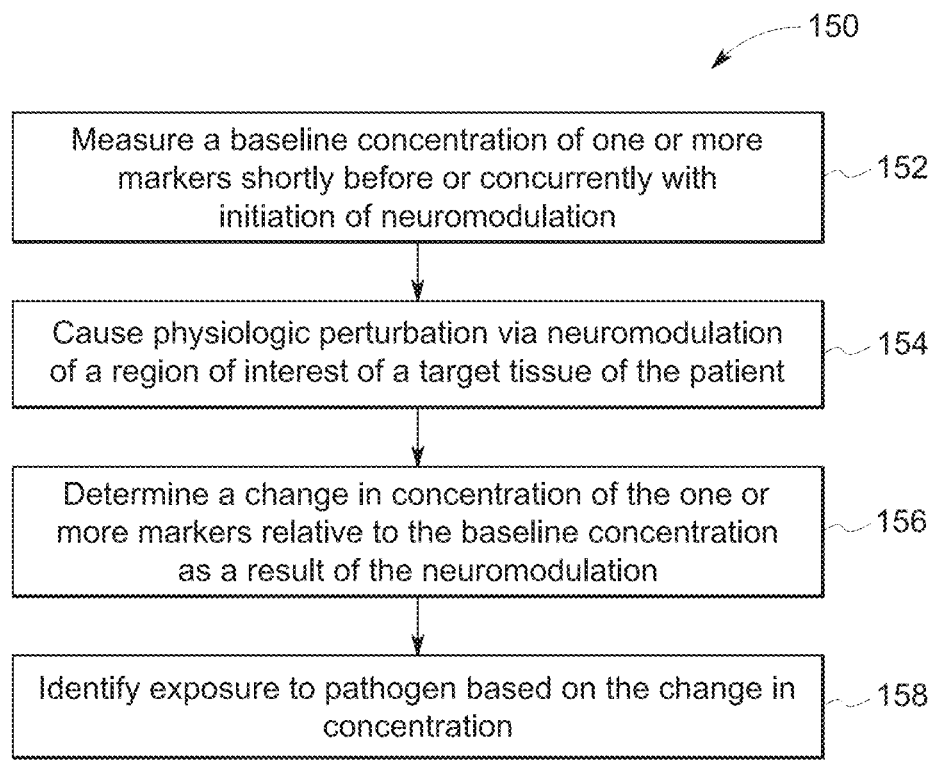
FIG. 18 is a flow diagram of a neuromodulation technique according to embodiments of the disclosure.

FIG. 18 is a flow diagram of a method 150 showing an immune response assessment technique for identifying pathogen exposure by assessing response to neuromodulation of a region if interest in an immune tissue or structure, including lymphatic organs, the lymph vessels that extend throughout the body and provide flow and drainage, the spleen, lymph nodes, Peyer's patches, and accessory lymphoid tissue (including the tonsils and appendix).

The technique acquires a baseline concentration of one or more markers, such as immune markers, at step 152, which may be at a time point immediately before (within 1-6 hours before) or concurrently with initiation of neuromodulation of a region of interest in a target tissue (e.g., spleen or immune tissue) at step 154. Based on the observed perturbation, which may be reflected in observing changes in one or more markers relative to baseline at step 156, a pathogen exposure may be identified at step 158. The change in concentration of one or more markers in response to neuromodulation that are associated with pathogen exposure or a lack of pathogen exposure may be identified according to the techniques provided herein (blood concentration, tissue concentration, system changes identified by sensor and/or image data).

Figure 19:
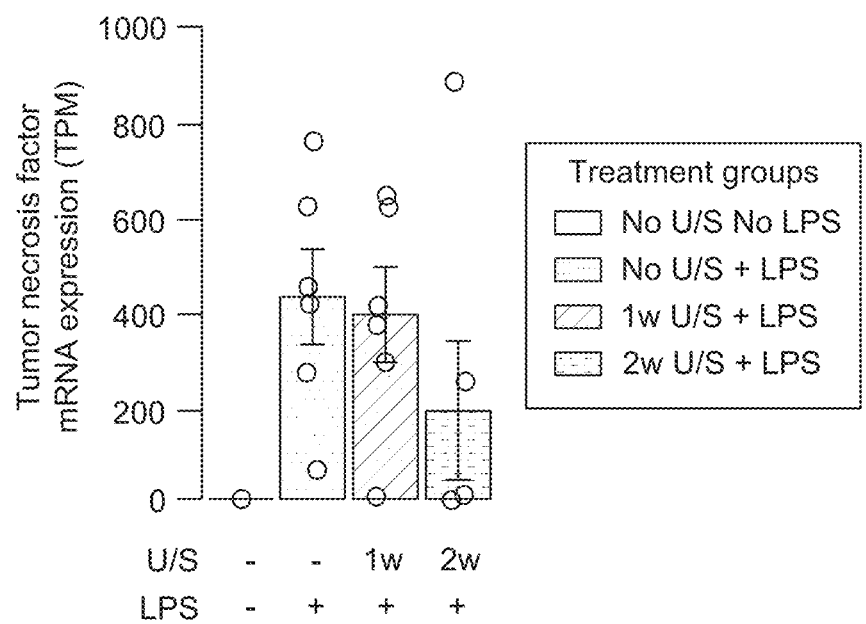
FIG. 19 shows TNF mRNA expression in treated vs. control groups after LPS exposure.
Figure 20:
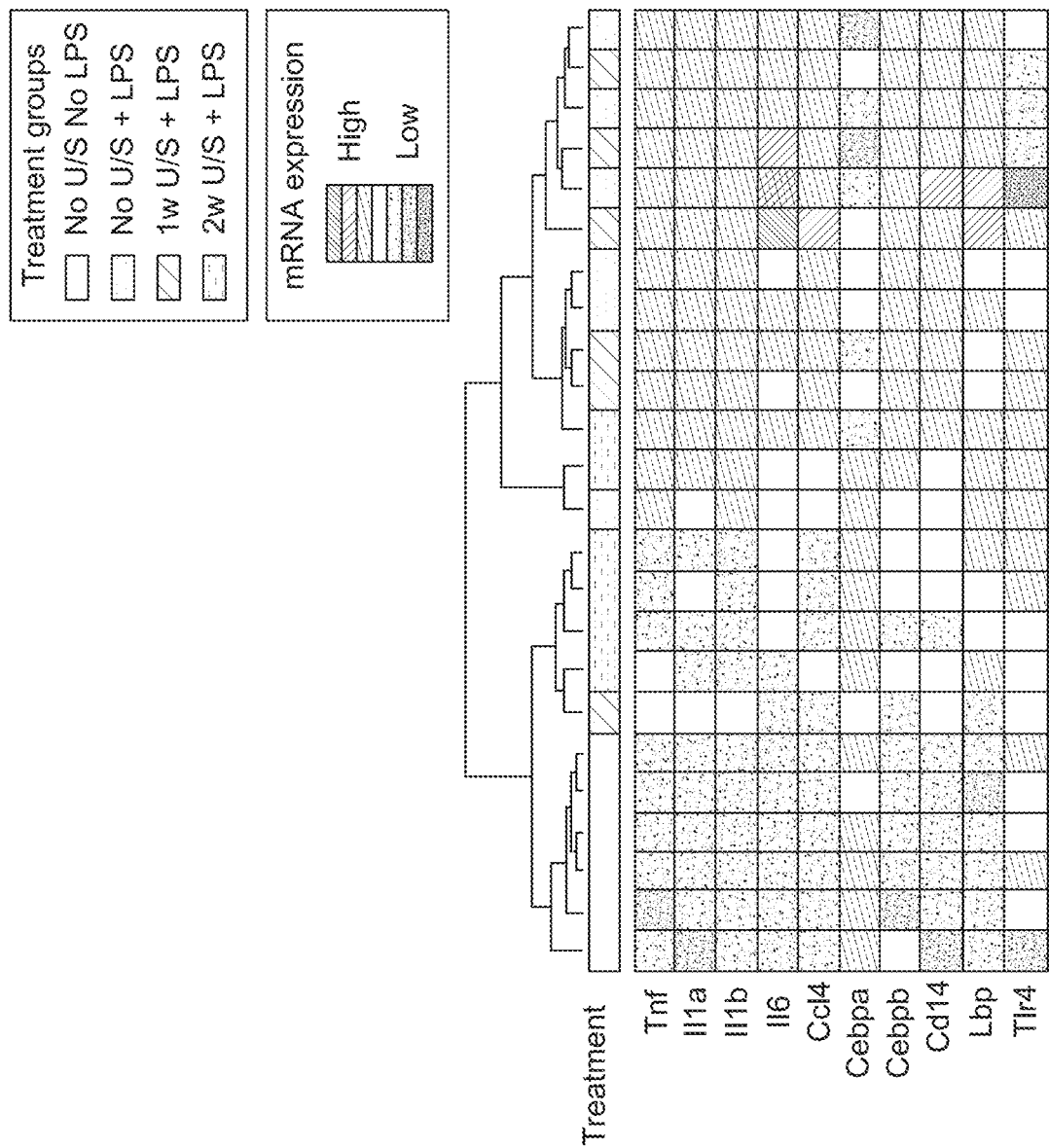
FIG. 20 shows mRNA expression for various markers in treated vs. control groups after LPS exposure.
Figure 21:
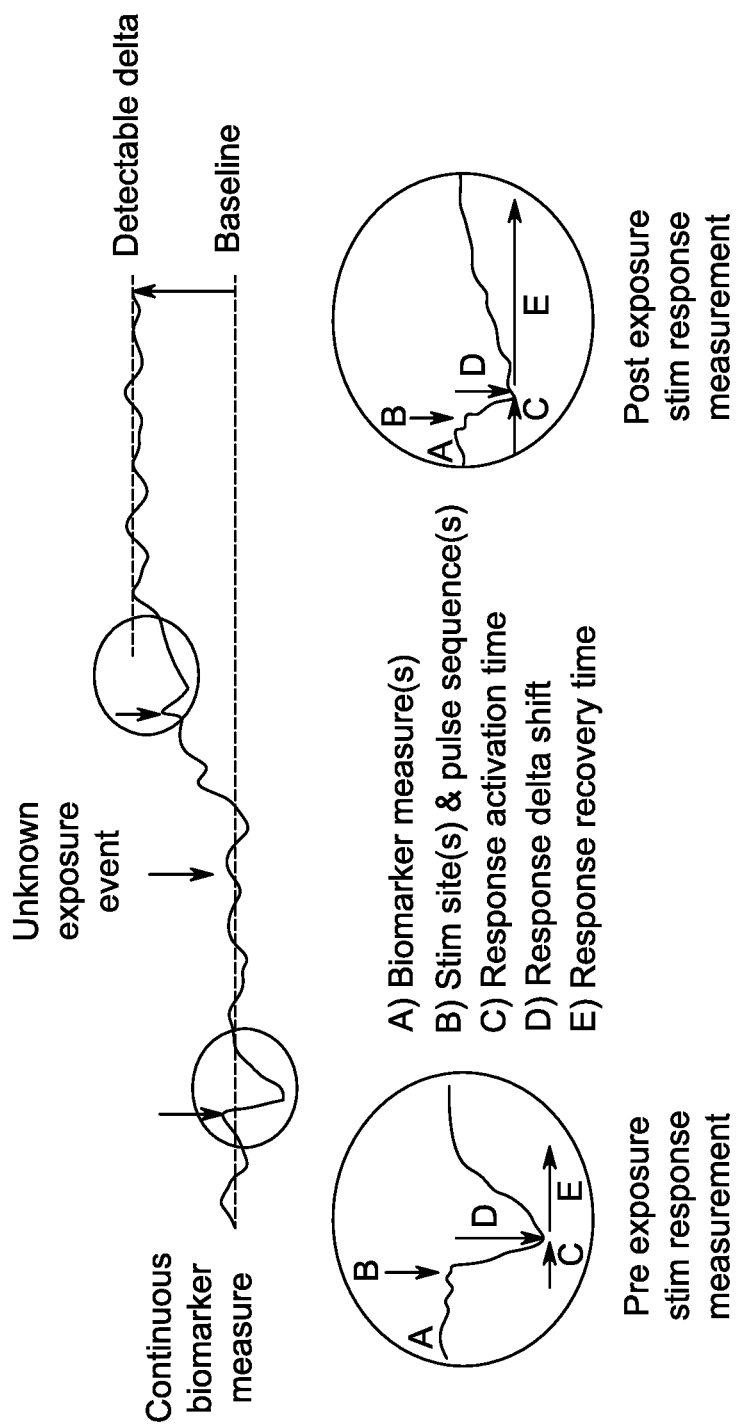
FIG. 21 shows an example protocol for acquiring baseline and potential post-exposure data for assessing a change in response based to neuromodulation after exposure to a material or pathogen.

FIG. 19 shows tumor necrosis factor mRNA expression changes that are ultrasound-dose dependent for animal subjects exposed to endotoxin or lipopolysaccharide (LPS) and treated with neuromodulating energy applied to the spleen. High dose treated animals experienced a largest decrease in tumor necrosis factor mRNA expression relative to control. FIG. 20 shows mRNA expression array data for a number of markers for control and LPS-exposed and high and low dose ultrasound treated animals. FIG. 21 shows an example protocol for acquiring baseline and potential post-exposure data for assessing a change in response based to neuromodulation after exposure to a material or pathogen. A baseline or characteristic pre-exposure response profile may be acquired and compared to a potential post-exposure response profile to assess changes driven by exposure.

The disclosed techniques as provided herein harness the targeted physiological outcomes that are achievable via neuromodulation. In addition to implementations in which the targeted physiological outcomes are used to treat subjects, these outcomes may be used as part of a diagnostic protocol. For example, application of energy to a region of interest in a target tissue may result in predictable and targeted physiological perturbations. One or more characteristics of the perturbations themselves or the subject's response to the perturbations may be indicative of a subject's clinical condition. For example, a rapid return to homeostasis (e.g., return to baseline pre-modulation concentrations of molecules of interest) within a pre-defined period of time may be indicative of a healthy response to the perturbation. In contrast, a slow response may be indicative of metabolic pathways that are underperforming relative to those in a healthy subject. While certain embodiments of the disclosure have been discussed in the context of glucose regulation, it should be understood that the present techniques may be used to cause perturbations of other systems (including acute or chronic inflammatory conditions and related sensory and neuroimmune effector systems) and, accordingly, to assess related clinical conditions.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A modulation system, comprising:
an energy application device configured to apply energy to a region of interest to cause a physiological perturbation in a subject; and
a controller configured to:
control application of the energy via the energy application device to the region of interest to induce the physiological perturbation to cause a change in concentration of one or more molecules of interest of the subject relative to a baseline concentration;
receive information indicative of the concentration of the one or more molecules of interest at one or more times points after the application of the energy; and
determine that the subject is in a category selected from a first category or a second category based on the change in the concentration of the one or more molecules of interest relative to the baseline concentration within a time period, wherein the first category is responsive to neuromodulation based on the change in the concentration being greater than a predetermined threshold and the second category is non-responsive to neuromodulation based on the change in the concentration being less than the predetermined threshold.

2. The system of claim 1, wherein the concentration is a glucose concentration received from an assessment device comprising a glucose monitor.

3. The system of claim 1, wherein the first category is reflective of exposure to a pathogen and wherein the second category is reflective of a lack of exposure to the pathogen, and wherein the region of interest is a spleen or immune tissue.

4. The system of claim 1, wherein the energy application device is an ultrasound probe.

5. The system of claim 1, wherein the system is configured to provide an indication of a neuromodulation treatment protocol upon determining that the subject is in the first category.

6. The system of claim 1, wherein the controller is configured to initiate a neuromodulation treatment protocol via the energy application device upon determining that the subject is in the first category.

7. The system of claim 6, wherein the neuromodulation treatment protocol comprises energy application to the region of interest.

8. The system of claim 7, wherein the region of interest is a liver, and wherein the one or more molecules comprises glucose.

9. The system of claim 7, wherein the region of interest is a spleen, and wherein the one or more molecules comprises a cytokine.

10. The system of claim 1, comprising an imaging transducer configured to generate image data of the region of interest.

11. The system of claim 10, wherein the energy application device comprises an ultrasound probe, and wherein the ultrasound probe comprises the imaging transducer.

12. The system of claim 1, wherein the region of interest comprises a pancreas, and wherein the subject is determined to be insulin resistant based on the change in concentration comprising an initial increase in circulating insulin that is higher than a predetermined insulin increase threshold at a first time point that is followed by a subsequent decrease in the circulating insulin relative to the initial increase at a second time point.

13. The system of claim 12, wherein the subject has baseline elevated circulating glucose or elevated circulating insulin.

14. The system of claim 12, wherein the subject is not fasted.

15. The system of claim 1, wherein the region of interest is tissue comprising axon terminals that form synapses with non-neuronal cells.

16. The system of claim 1, wherein the region of interest is gastrointestinal tissue.

17. The system of claim 1, wherein the controller is configured to control application of the energy via the energy application device to the region of interest to induce the physiological perturbation to cause a change in gene expression, tissue displacement, tissue size changes, cell migration, or any combination thereof.

* * * * *